(12) United States Patent
Melnyk et al.

(10) Patent No.: US 8,178,474 B1
(45) Date of Patent: May 15, 2012

(54) FUNCTIONALISED SOLID SUPPORT FOR ALPHA-OXOALDEHYDE SYNTHESIS

(75) Inventors: Oleg Melnyk, Mons-En-Baroeul (FR); Jean-Sebastien Fruchart, Lievin (FR); Line Bourel, Lille (FR); Helene Gras-Masse, Merignies (FR)

(73) Assignees: Institut Pasteur de Lille, Lille (FR); Centre National de la Recherche Scientifique CNRS, Paris (FR)

( * ) Notice: Subject to any disclaimer, the term of this patent is extended or adjusted under 35 U.S.C. 154(b) by 2217 days.

(21) Appl. No.: 10/196,900

(22) Filed: Jul. 15, 2002

Related U.S. Application Data

(63) Continuation of application No. 09/959,194, filed as application No. PCT/FR00/01035 on Apr. 21, 2000, now abandoned.

(30) Foreign Application Priority Data

Apr. 21, 1999 (FR) ..................................... 99 05024

(51) Int. Cl.
*C40B 50/18* (2006.01)
(52) U.S. Cl. .............. 506/32; 435/86; 514/1.1; 530/334
(58) Field of Classification Search ........................ None
See application file for complete search history.

(56) References Cited

U.S. PATENT DOCUMENTS 5,362,852 A 11/1994 Geoghegan

FOREIGN PATENT DOCUMENTS

WO WO 94/25071 11/1994

OTHER PUBLICATIONS

Grandjean et al., "One-Pot Synthesis of Antigen-Bearing, Lysine-Based Cluster Mannosides Using Two Orthogonal Chemoselective Ligation Reactions" Angew. Chem. Int. Ed. 2000, 39, 6, 1068-1072.*
Melnyk et al., "Functionalization of Peptides and Proteins by Aldehyde or Keto Groups" Biopolymers 2000, 55, 165-186.*
Fruchart et al. "A new linker for the synthesis of C-terminal peptide α-oxoaldehydes" Tetrahedron Letters Aug. 20, 1999, 40, 6225-6228.*
Brase et al., "A Surprising Solid-Phase Effect: Development of a Recyclable 'Traceless' Linker System for Reactions on Solid Support" Angew. Chem. Int. Ed. Dec. 31, 1998, 37(24), pp. 3413-3415.*
Bohm et al., "A novel linker for the attachment of alcohols to solid supports" Tetrahedron Letters 1998, 39, 3810-3822.*
Lynas, J.F., "Inhibitors of the chymotrypsin . . . ", *Bioorganic & Medicinal Chemistry Letters*, vol. 8, No. 4, 1998, pp. 373-378.
Geoghegan, K.F., "Site-directed conjugation of nonpeptide groups to peptides . . . ", *Bioconjugate Chemistry*, vol. 3, 1992, pp. 138-146.
Zhang, L., "Preparation of functionally active cell-permeable peptides . . . " *Proceedings of the Nat'l Academy of Sciences of USA*, vol. 95, No. 16, Aug. 4, 1998, pp. 9184-9189.
Fruchart, J.S., "A new linker for the synthesis . . . ", *Tetrahedron Letters*, vol. 40, No. 20, Aug. 20, 1999, pp. 6225-6228.

* cited by examiner

*Primary Examiner* — Christopher M Gross
(74) *Attorney, Agent, or Firm* — Birch, Stewart, Kolasch & Birch, LLP

(57) ABSTRACT

The invention relates to a functionalised solid support for the synthesis of compounds comprising at least one α-oxoaldehyde function, to a process for preparing it and to its applications, in particular for the preparation of a library of organic compounds, of a diagnostic reagent, of a microtitration plate and of a biochip, such as a DNA chip. The present invention also relates to a process for the synthesis of organic compounds comprising at least one α-oxoaldehyde function and to the α-oxoaldehyde peptides obtained using this process.

10 Claims, 11 Drawing Sheets peptide 19 peptide 21 (SEQ ID NO: 8)

FUNCTIONALISED SOLID SUPPORT FOR ALPHA-OXOALDEHYDE SYNTHESIS

This application is a continuation of application Ser. No. 09/959,194, filed on Oct. 19, 2001 now abandoned for which priority is claimed under U.S.C. §120. Application Ser. No. 09/959,194 is the National Phase of PCT Application No: PCT/FR00/01035 filed on Apr. 21, 2000 under 35 U.S.C. §371. The entire contents of each of the above-identified applications are hereby incorporated by reference. This application also claims priority to Application No: 99 05024 filed in France on Apr. 21, 1999 under 35 U.S.C. §119.

The present invention relates to functionalised solid supports for solid phase organic syntheses, to a process for preparing them and to their applications, in particular to the synthesis of α-oxoaldehyde peptides or other organic molecules, such as the non-peptidic derivatives of glyoxylic acid.

The present invention also relates to α-oxoaldehyde peptides, to a process for preparing them using said functionalised supports and to their applications, in particular in the pharmaceutical industry, for example in the field of synthetic vaccines or of the synthesis of macromolecules obtained by chemical ligation (the coupling of several molecular fragments thanks to the use of chemoselective reactions), or again, of the creation of combinatorial libraries, of micro-titration plates or of biochips, such as DNA chips.

The automated synthesis of organic molecules and, in particular, the solid phase synthesis of peptidic macromolecules was initially developed by Merrifield. The general pattern of the reaction is as follows: the bonding of a first N-protected amino acid to a functionalised insoluble solid support, deprotection of the terminal amine function, extension of the chain (successive coupling of different amino acids), possibly deprotection of the N-terminal amino acid and then, simultaneously, cleavage the polypeptide from the resin and deprotection of the side chains of the amino acids.

Various types of insolubilised solid supports have been proposed: polystyrenes, polymethacrylates, polysaccharides, phenolic resins, silicon dioxide, porous glass and polyacrylamides; the supports most used are polyacrylamides and polystyrenes, more particularly poly(styrenes-co-divinylbenzenes).

To be efficient and to provide an adequate yield, solid support synthesis depends on several factors: the choice of functionalised resin, the choice of amino acid protecting groups, the choice of reaction conditions and the choice of the different peptides that can be combined to obtain the desired final product.

However, presently used resins do not permit direct generation of the final product; for example, a product bearing an α-oxoaldehyde function, from the anchoring function on the solid support. In the case of the synthesis of peptides comprising an α-oxoaldehyde function, the resins habitually used do not enable the α-oxoaldehyde peptide to be obtained other than in the form of a precursor which will have to undergo a subsequent transformation in homogenous phase to generate the desired function.

At the present time, peptidic structures of a large size can be obtained by chemical ligation, in an aqueous or partially aqueous medium, of partially protected or totally de-protected peptidic fragments, obtained in advance by solid phase synthesis using conventional resins.

This method brings into play a covalent bond of the amide, thioester, thioether, thiazolidine, oxime or again, hydrazone type, between two suitably functionalised peptidic fragments. In particular, thiazolidine, oxime and hydrazone bonds necessitate the preparation of peptides having aldehyde functions.

Geohegan, K. F. et al. (Bioconjugate Chem., 1992, 3, 138-146) have described peptides bearing an aldehyde function in N-terminal position, obtained by periodic oxidation, in homogenous phase, of a serine or a threonine in N-terminal position (presence of a β-aminoalcohol). The N-terminal α-oxoaldehyde function obtained is highly reactive vis-à-vis 1,2-aminothiol, hydroxylamine or hydrazine functions of other peptidic fragments, permitting their coupling.

This method necessitates the preparation of the β-aminoalcohol, its purification, its oxidation and, finally, separation of the product from the oxidation reagents.

The use of β-aminoalcohols is also described in U.S. Pat. No. 5,362,852: an α-oxoaldehyde function is generated, in a peptide, by periodic oxidation in homogenous phase of a 2-hydroxylamine present in the peptide chain, which is the case either in peptides bearing a serine or a threonine in N-terminal position, or in peptides into which a hydroxylysine group has been inserted.

Similarly, International PCT Application WO 94/25071 describes the formation of an α-oxoaldehyde function at the N-terminal end of a peptide, by periodic oxidation in homogenous phase of a peptide bearing a serine or a threonine at said N-terminal end. Said peptide is synthesised in an automated manner using a SASRIN® resin, supplied by Bachem.

As to the creation of an aldehyde function in C-terminal position, there exist only a few methods; some of these necessitate the formation of α-aminoaldehyde functions in C-terminal position. The resulting peptides have the drawback of being unstable and, among other things, of being subject to epimerisation reactions.

J. P. TAM et al. (Proc. Natl. Acad. Sci., August 1998, 95, 9184-9189) have proposed the synthesis of peptides bearing a glycoaldehyde group (—NH—CH$_2$—CHO) in C-terminal position. The synthesis described is impractical: it necessitates the preparation of a spacer, as well as the formation of the aldehyde function in homogenous phase. The solid phase is used only for solid phase recurring peptide synthesis. This synthesis cannot be automated as the final step takes place in homogenous phase.

The introduction of an α-oxoaldehyde function in C-terminal position is described in aforementioned International PCT Application WO 94/25071, said function not being directly linked, however, with the peptidic backbone, as apparent from the process used: a peptide chain is solid phase synthesised, using a polystyrene type resin, a sequence of five lysines being inserted in C-terminal position; serines are grafted onto the α (N-terminal ends of the peptide) or ε (side chains of the lysines) free amine functions; the peptide thus modified is separated from the solid support; a periodic oxidation in homogenous phase permits the formation of α-oxoaldehyde functions in N-terminal position and at the side chains of the lysines present at the C-terminal end.

J. P. TAM et al (Proc. Natl. Acad. Sci., August 1998, 95, 9184-9189) have also described, in a similar way, the insertion of a lysine residue in C-terminal position of a peptide obtained in solid phase, the grafting of a serine residue onto the amine function of the lysine side chain, the cleavage of the peptide from the support and periodic oxidation, in homogenous phase, of the β-aminoalcohol present in said serine, to obtain an α-oxoaldehyde function.

In all these methods, the functionalisation of the peptides by an aldehyde function takes place in homogenous phase, after the peptide has been cleft from the solid support.

There is thus a clear need for a simple, automatable method of synthesis of organic products having an α-oxoaldehyde function, such as peptides bearing an α-oxoaldehyde function, in C-terminal position for example, for the purpose of using them, for example, as enzyme inhibitors or as products of pharmaceutical or pharmacological interest, or in the framework of chemical ligation for the preparation of more complex structures, as well as for a support suitable for the implementation of this method.

The inventors have thus set themselves the task of providing a solid support suitable for the chemical modification of organic molecules by α-oxoaldehyde functions, as well as a process for the synthesis of compounds comprising at least one α-oxoaldehyde function, said process meeting the following requirements:

it must permit the formation of the α-oxoaldehyde function in a single step, during separation of the product from the solid support, the step of cleavage of the product from the solid support must directly generate the final product, that is to say, in the case of a peptide synthesis, the α-oxoaldehyde peptide in a de-protected form, the process must make use of low-cost reagents, be efficient (good yield), simple and possible to automate.

The object of the present invention is thus a functionalised solid support for the synthesis of compounds comprising at least one α-oxoaldehyde function, which support is characterised in that it corresponds to the following formula I:

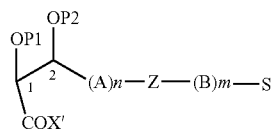

wherein:
S represents a solid support of which at least the surface has the property of being well solvated in an aqueous or partially aqueous medium;
n and m, which can be identical or different, represent 0 or 1;
Z represents a functional group selected from the group constituted by ether, thioether, ester, amine, amide, sulfonamide, hydroxylamine, hydrazine, hydrazone, thiazolidine, oxime, carbonate, carbamate, thiocarbamate, urea, thiourea functional groups and their derivatives when n is equal to 1;
Z represents a functional group selected from the group constituted by the ester, amide, N-acylhydroxylamine, hydrazide, hydrazone, oxime and thiazolidine functional groups and their derivatives when n is equal to 0;
P1 and P2, which can be identical or different or form together a ring with the oxygen atoms to which they are bound, represent hydrogen atoms or functional groups protecting the hydroxyl functions in positions 1,2, P1 and P2 being, in this case, selected from the groupe constituted by the —$R_1$, —(CO)$R_1$, —(CO)O$R_1$, —($SO_2$)O$R_1$, —SiR'R"R'", acetal and cetal functional groups, $R_1$, R', R" and R'" representing linear, branched or cyclic, saturated or unsaturated, alkyl groups including from 1 to 18 carbon atoms, or aryl or heteroaryl groups, said alkyl, aryl or heteroaryl groups being possibly partially or completely substituted by one or more halogen atoms, one or more amino, hydroxy, alcoxy, aryloxy, alkylthio or arylthio groups;
A and B, which can be identical or different, represent a linear, ramified or cyclic, saturated or unsaturated, carbon chain, comprising from 1 to 18 carbon atoms and, possibly, from 1 to 7 functional groups selected from the group constituted by the carbonyl functional groups, the carbocycles, heterocyclic compounds, aryls and heteroaryls, with A and/or B possibly further comprising from 1 to 16 hetero atoms, preferably from 1 to 16 nitrogen or oxygen atoms, and being substitutable by 1 to 16 hydroxyl or amino functional groups, possibly suitably protected,
at least one of the carbon atoms of A and/or B being possibly substituted by a functional group:

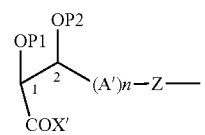

wherein A' is identical with or different from A; in the latter case, A' is selected from among the other A functional groups defined hereabove; and
X' is selected from the group constituted by the —O$R_1$, —NR'R" groups, $R_1$, R' and R" representing a hydrogen atom or being as defined hereabove.

By way of example and non-limitatively:
suitable alkyl groups are methyl, ethyl, propyl, isopropyl, tert-butyl, vinyl, allyl or benzyl groups;
suitable aryl groups (aromatic cycles) are phenyl or cresyl groups;
suitable heteroaryl groups (aromatic heterocyclic compounds) are pyridine, pyrimidine or pyrazine groups;
suitable carbocycles are cyclopentyl or cyclohexyl groups;
a suitable heterocyclic compound is a piperazine group.

Halogen atoms that can substitute said alkyl, aryl or heteroaryl groups are, for example, fluorine, chlorine or bromine. Suitable alcoxy groups are, for example, methoxy, ethoxy, propoxy, isopropoxy, vinlyoxy and alloxy groups; suitable aryloxy groups are, for example, phenoxy or cresyloxy families; suitable alkylthio groups are, for example, methylthio, ethylthio, propylthio or vinylthio groups; suitable arylthio groups are, for example, phenylthio or cresylthio groups.

By way of example and non-limitatively, protective groups P1 and P2 can be as follows:
when P1 and P2 represent a —$R_1$ functional group, the latter can be methyl, tert-butyl, paramethoxybenzyl, methoxymethyl, benzyloxymethyl, paramethoxybenzyloxymethyl, paramethoxyphenoxymethyl, tert-butoxymethyl, 4-penteneyloxymethyl, sylyloxymethyl, 2-methoxyethoxymethyl, 2-(trimethylsilyl)-ethoxymethyl, triphenylmethyl, tetrahydropyranyl, guaiacolmethyl, etc.;
when P1 and P2 represent a —(CO)$R_1$ functional group, the latter can be acetyl, benzoyl, paramethylbenzoyl, pivaloyl, etc.;
when P1 and P2 represent a —(CO)O$R_1$ functional group, the latter can be a —COOCH$_3$, —COOC$_2$H$_5$, —COOCH$_2$C$_6$H$_5$, 9-fluorenylmethoxycarbonyl, etc.;
when P1 and P2 represent a —(SO$_2$)O$R_1$ functional group, the latters can be a —(SO$_2$)OCH$_3$, —(SO$_2$)OC$_2$H$_5$ functional group, etc.;
when P1 and P2 represent a —SiR'R"R'" functional group, the latter can be a trimethylsilyl, triethylsilyl, triisopropylsilyl, tert-butyldimethylsilyl, tert-butyldiphenylsilyl functional group, etc.;
when P1 and P2 represent an acetal or a cetal functional group, the latters can be benzylidene, isopropylidene, etc.

Alternatively, when P1 and P2 form together a cycle with the oxygen atoms to which they are bound, this cycle can be 1,3,2-dioxathiolane.

It is to be clearly understood, however, that any protective group of an hydroxyl function can be used as a P1 or P2 group, as described, for example, in "*Protective Groups in Organic Synthesis*", Theodora W. Greene and Peter G. M. Wuts, 1991, John Wiley and Sons, Inc.

Surprisingly, such functionalised supports according to the present invention are particularly suitable for the preparation of compounds comprising at least one α-oxoaldehyde function, and this being without prior synthesis of an aldehyde.

Furthermore, they have numerous advantages:
specificity of the cleavage of the synthesised compound from the support, under mild conditions;
compatibility with numerous organic molecules;
possibility of recycling the initial support, as explained in detail below.

According to a preferred embodiment of said support S, it is selected from the group constituted by:
particles of porous borosilicate glass;
surfaces made of glass or silicon;
resins selected from the group constituted by polyacrylamide resins, polyacrylamide-polyethylene glycol resins, polyethylene glycol-polystyrene resins, cross-linked ethoxylate-acrylate resins and polyethylene, polystyrene or polypropylene type resins grafted by hydrophilic molecules.

Such resins are commercially available under the trade names SPAR® (polyacrylamide type resin), PEGA® (polyacryalamide-polyethylene glycol type resin), TENTAGEL®, ARGOGEL®, NOVASYN®, NOVAGEL® (polyethylene glycol-polystyrene type resins), CLEAR® (cross-linked ethoxylate-acrylate resin, CHIRON®, SYNPHASE-MD® (polyethylene ring grafted by a methacrylic/dimethylacrylamide acid copolymer), SYNPHASE-HM® (ring of polyethylene grafted by hydroxyethyl-methacrylate), etc.

A suitable glass surface is, for example, a microscope slide.

A preferred formula I support according to the present invention is, for example, such that S is a polyacrylamide-polethyleneglycol type resin, m and n represent 1, B is a —(CH₂)₂—CO—NH— chain, Z is an amide functional group, A is a —CO—NH—(CH₂)₃— chain, P1 and P2 form together an isopropylidene protective functional group and X' represents a —NH—(CH₂)₃—NH₂ chain.

Another preferred formula I support according to the present invention for example, such that S is a polyacrylamide-polyetheyleneglycol or polyethyeleneglycol-polystyrene type resin, m and n represent O, Z is an amide group, P1 and P2 form together an isopropylidene protective group and X' represents a methoxy group.

Another preferred formula I support according to the present invention corresponds, for example, to formula I, in which S is as defined above, m represents 1, n represents O, Z is an amide functional group, P1 and P2 form together an isopropylidene protective group, X' represents a methoxy group and B represents the following group:

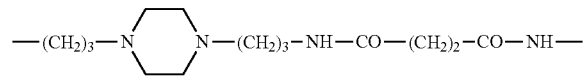

Another preferred formula I support according to the present invention corresponds, for example, to formula I, in which S is as defined above, m and n represent 1, Z is an amide group, P1 and P2 form together an isopropylidene protective group, B is a —(CH₂)₂—CO—NH— group, A represents the following group:

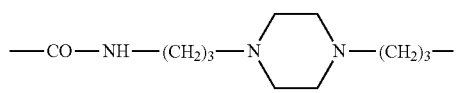

and x' represents the following group:

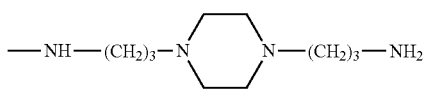

Another preferred formula I support according to the present invention corresponds, for example to formula I, in which S is as defined above, m represents 0, n represents 1, Z is a carbamate group, P1 and P2 form together an isopropylidene protective group, X' represents a methoxy group and A represents the following group:

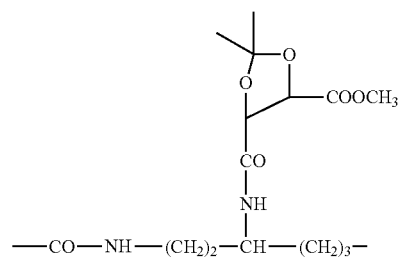

Another preferred formula I support according to the following invention corresponds, for example to the following formula:

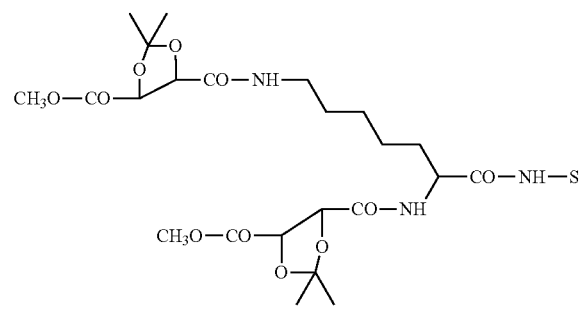

wherein S is as defined above, n=0, m=1, Z is an amide functional group, X' represents a methoxy group, P1 and P2 form together an isopropylidene group and B represents a group:

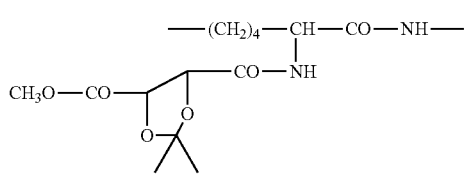

Another preferred formula I support according to the present invention corresponds, for example, to the following formula:

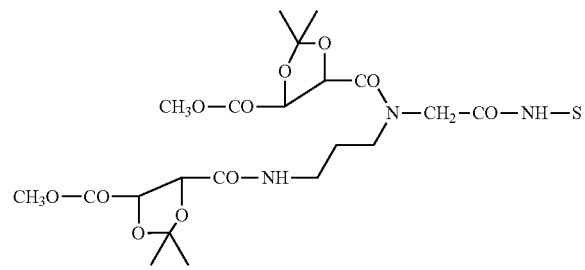

wherein S is as defined above, n=0, m=1, Z is an amide functional group, X' represents a methoxy group, P1 and P2 together form an isopropylidene group and B represents a group:

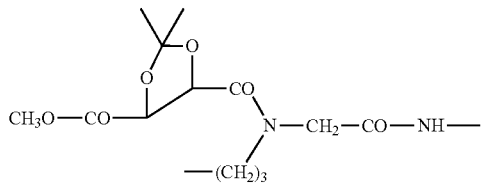

The formula I supports according to the invention can advantageously be used as solid supports for the synthesis of α-oxoaldehyde peptides or of other organic molecules functionalised by at least one α-oxoaldehyde, such as the derivatives of glyoxylic acid.

The formula I supports according to the invention can also be used for the synthesis of oligonucleotides, in particular oligodeoxynucleotides, or of lipids functionalised by at least one α-oxoaldehyde, using well-known techniques, described, for example, in "*Oligonucleotide synthesis: a practical approach*", 1984, M. J. GAIT Ed., IRL Press, Washington D.C. The formula I supports according to the present invention can also be used for the solid phase synthesis of peptides or of proteins in an automated manner, as described, for example, by R .C. Sheppard in Comp. Org. Chem., 1979, 5, 352-355 and by R. B. Merrifield in Science, 18$^{th}$ April 1986, 232, 341-347. During such a synthesis, the side chains of the amino acids are suitably protected, as known per se.

The present invention also relates to a process for preparing the formula I support described above, said process being characterised in that it consists in reacting:
a functionalised solid support having the formula S—(B)$_m$—Y, wherein B, S and m are as described above and Y represents a nucleophilic group, B being substitutable by at least one other Y functional group, identical with or different from the one represented in the formula S—(B)$_m$—Y, in addition to the one represented in the formula S—(B)$_m$—Y, in which case said solid support is polyfunctionalised,
with a compound selected from the group constituted by the cyclic anhydrides of tartaric acid or of one of its derivatives and the compounds of formula II:

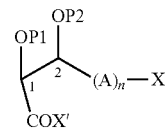

wherein n, A, P1, P2 and X' are as defined above and X represents an electrophilic group.

According to the sense of the present invention, "nucleophilic" is to be taken as meaning a group having a pair of free electrons, that is to say an electron donor group. "Electrophilic" is to be taken as meaning a group having a low-energy vacant molecular orbital capable of interacting with the pair of free electrons of the nucleophilic group, that is to say an electron acceptor group.

Alternatively, in the event of n=1, Y can represent an electrophilic group and X can represent a nucleophilic group.

According to one advantageous form of embodiment of said process according to the present invention, a suitable electrophilic group (that is to say the group X in the event of n=0, and the group X or the group Y in the event of n=1) is preferably selected from the group constituted by the following functional groups:

when n=1: —CR$_2$R$_3$Cl, —CR$_2$R$_3$Br, —CR$_2$R$_3$I, —CR$_2$R$_3$OSO$_2$R$_4$, —CHO, —COOR$_2$, —COF, —COCl, —COBr, —SO$_2$OR$_2$, —SOOCl, succinimidyl ester, sulphosuccinimidyl ester, —COO$^-$ transformed by an electrophilic activating agent, —N=C=O (isocyanate), —N=C=S (isothiocyanate), —O—CO—OR$_2$, —O—-CO-Im, —O—COCl, —NR$_2$-COCl and —NR$_2$—CO—Im, wherein Im represents a possibly substituted imidazolyl group of the formula:

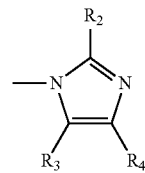

and where R$_2$, R$_3$ and R$_4$, which can be identical or different, represent hydrogen atoms or linear, branched or cyclic, saturated or unsaturated, alkyl groups including from 1 to 18 carbon atoms, or aryl or heteroaryl groups, said alkyl, aryl and heteroaryl groups being possibly partially or completely substituted by one or more halogen atoms, one or more amino, hydroxy, alcoxy, aryloxy, alkylthio or arylthio groups;

when n=0: —CHO, —COOR$_2$, —COF, —COCl, —COBr, —COO$^-$ transformed by an electrophilic activating agent, R$_2$ being as described above in the case of n=1.

An electrophilic activating agent is an agent which, reacting with carboxylate —COO$^-$, imparts thereto an electrophilic nature. Such an agent is well-known to those skilled in the art and is, for example, described in "*Comprehensive organic synthesis*", B. M. Trost and I. Fleming Ed., Pergamon Press, 1991, volumes 1-9.

According to another advantageous embodiment of said process, a suitable nucleophilic group (that is to say group Y in the event of n=0, and group X or group Y in the event of n=1) is preferably selected from the group constituted by the following functional groups when n=0 or when n=1:

—OH, —SH, —COO⁻, —NHR₅, —CONR₅NH₂, —N[R₅(CO)]NH₂, —N[R₅O(CO)]NH₂, —N[R₅NH(CO)]NH₂, —SO₂NH₂, —SO₂NR₅NH₂, —ONH₂, —(CO)ONH₂ and —C(NHR₅)—CR₅R₆—SH, R₅ and R₆ having the same meaning as R₂ to R₄ groups defined above in the case of the electrophilic groups.

According to one advantageous embodiment of the process for preparing the formula I support, in the event of n=0 and X=—COOR₂, with R₂=H, this group can play the part both of a nucleophilic and of an electrophilic group. In the event of n=0 and of X=—COOH, X can thus represent a nucleophilic group and Y an electrophilic group. For example, if X=—COOH and Y=—NHR₅, X plays the part of an electrophilic group. On the other hand, if X=—COOH and Y=—CR₂R₃Cl, —CR₂R₃Br, —CR₂R₃I or —CR₂R₃OSO₂R₄, then X plays the part of a nucleophilic group.

Thus the reaction of the solid support S—(B)ₘ—Y with a cyclic anhydride of tartaric acid, or of one of its derivatives, or with the compound of formula II makes it possible to obtain the support of formula I according to the invention. Depending on the X and Y functional groups chosen, different Z groups can be formed. By way of example, and non-limitatively:

- a Z functional group=ether (thioether or amine, respectively) can be formed by reaction of X=—OH (—SH or —NHR₅, respectively) with Y=—CR₂R₃Cl, —CR₂R₃Br, —CR₂R₃I or —CR₂R₃OSO₂R₄ (for example a tosylate or a mesylate);
- a Z functional group=ester (amide, respectively) can be formed by reaction of X=—OH (—NHR₅, respectively) with Y=—COOR₂, —COF, —COCl or COBr;
- a Z functional group=sulfonamide can be formed by reaction of X=—NHR₅ with Y=—SO₂OR₂ or —SOOCl;
- a Z functional group=hydroxylamine or a hydroxylamine derivative, such as an N-acylhydroxylamine or N,O-acylhydroxylamine bond, can be formed from X=—ONH₂ or —(CO)ONH₂ with Y=—COOR₂, —COF, —COCl, —COBr, —SO₂OR₂ or —SOOCl;
- a Z functional group=hydrazine or hydrazine derivative can be formed by reaction of X=—CONR₅NH₂, —N[R₅(CO)]NH₂, —N[R₅O(CO)]NH₂, —N[R₅NH(CO)]NH₂ or —SO₂NR₅NH₂ with Y=—COOR₂, —COF, —COCl, COBr, SO₂OR₂ or —SOOCl;
- a Z functional group=hydrazone or its derivatives (for example sulphonylhydrazone) can be formed by the reaction of X=—CONR₅NH₂, with Y=—CHO;
- a Z functional group=thiazolidine can be formed between X=—C(NHR₅)—CR₅R₅—SH and Y=—CHO;
- a Z functional group=oxime can be formed by reaction between X=—ONH₂ and Y=—CHO;
- a Z functional group=carbonate (—O—CO—O—) can be formed by reaction between X=—O—CO—OR₂, —O—CO-Im or —O—COCl and Y=—OH;
- a Z functional group=carbamate (—NR₂—CO—O—) can be formed by reaction between X=—NR₂—COCl, —NR₂—CO—Im or isocyanate and Y=—OH, or again, between X=—O—CO—OR₂, —O—CO—Im or —O—COCl and y=—NHR₅;
- a Z functional group=thiocarbamate (—NR₂—CS—O—) can be formed between X=isothiocyanate and Y=—OH;
- a Z functional group=urea can be formed between X=—NR₂—CO—Im, —NR₂—CO—Im or isocyanate and Y=—NHR₅;
- a Z group=thiourea can be formed between x=isocyanate and Y=—NHR₅

According to one advantageous embodiment of the process for preparing the formula I support according to the invention, said cyclic anhydride of tartaric acid or of its derivatives is di-O-benzoyl-tartaric anhydride or diacetyl-tartaric anhydride.

According to another advantageous embodiment of the process for preparing the formula I support according to the invention, when P1 and P2 represent a hydrogen atom when the solid support having the formula S—(B)ₘ—Y reacts with the formula II compound, P1 and P2 groups other than hydrogen atoms, namely groups protecting hydroxyl functions in positions 1,2 can possibly be introduced after the reaction of the solid support having the formula S—(B)ₘ—Y with the formula II compound, and before the formula I support according to the invention is used for the synthesis of compounds comprising at least one α-oxoaldehyde function.

According to yet another advantageous form of embodiment of the process according to the invention, the formula II compound represents tartaric acid or a derivative of tartaric acid. In this case, the reaction between the solid support S—(B)ₘ—Y and the formula II compound corresponds, when group A of the formula II compound is such that it comprises a carbonyl function in alpha position of the —OP2 group, to the grafting of tartaric acid or of a derivative of tartaric acid on the solid support S—(B)ₘ—Y.

One such derivative of tartaric acid is, for example, and non-limitatively:

- a salt of tartaric acid (sodium, lithium salt),
- dibenzoyl-tartaric acid,
- di-paratoluoyl-tartaric acid,
- diisopropyl-tartaric acid,
- dipivaloyl-tartaric acid,
- diacetyl tartaric acid,
- metatartaric acid,
- cichorinic acid,
- tartralinic acid,
- 4-fluoro-tartranilic acid,
- 4-chloro-tartranilic acid,
- 4-methyl-tartranilic acid,
- 4-nitro-tartranilic acid,
- tartaric acid mono-N-octylamide,
- N-(2,4-dichlorophenyl)-2,3-dihydroxy-succinamic acid,
- 2,3-diacetoxy-N-[1-(1-naphthyl)ethyl] succinamic acid,
- 4-acetoxy-2,5-dioxo-tetrahydro-furan-3-yle acetate,
- 3,4-dihydroxy-2,5-dioxotetrahydrofuran di-para-toluate,
- dimethyl tartrate,
- diethyl tartrate,
- dibutyl tartrate,
- ditert-butyl tartrate,
- diisopropyl tartrate,
- disuccinimidyl tartrate,
- disulphosuccinimidyl tartrate,
- diisoamyl tartrate,
- dibenzyl tartrate,
- 3-pyridylmethyl tartrate,
- dimethyl 2,3-O-isopropylidene tartrate,
- dimethyl 2,3-O-benzylidene tartrate,
- dimethyl 2,3-O-(1-phenylethylidene) tartrate,
- diethyl 2,3-O-isopropylidene tartrate,
- dimethyl 2,3-O-benzylidene tartrate, diisopropyl O,O'-bis(trimethylsilyl) tartrate,
phenylpropanolamine bitartrate,
nicotinylic alcohol bitartrate,
dimethyl 1,3,2-dioxathiolane 4,5-dicarboxylate,
diethyl 2-phenyl-1,3-dioxolane 4,5-dicarboxylate,
dimethyl 2-phenyl-1,3-dioxolane 4,5-dicarboxylate,
dibenzyl 2,3-dihydroxysuccinate,
di[2-oxo-2-(4-(trifluoromethyl)phenyl)ethyl] 2,3-dihydroxysuccinate.

During the time of the reaction between the solid support S—(B)$_m$—Y with the cyclic anhydride of tartaric acid (or one of its derivatives) or the formula II compound, and when the formula II compound is an ester of tartaric acid or (or of one of its derivatives), said cyclic anhydride or said ester may possibly be subjected to a hydrolysis or saponification reaction prior to its reaction with said solid support, the purpose of this being to generate a free acid function that is reactive with the functionalised solid support.

According to another advantageous embodiment of the process according to the present invention, the formula II compound is selected from the group constituted by mucic acid, saccharic acid, glucaric acid (in which cases, X'=—OH, n=1, A=—CH(OH)—CH(OH)—, X=—COOH, P1=P2=H in formula II, with the three acids being distinguished by their respective stereochemistries), their salts (potassium, calcium) and their derivatives.

According to yet another advantageous embodiment of the process according to the present invention, said process consists in reacting:

a functionalised solid support having the formula:

wherein S is as previously defined,
with a dimethyl-2,3-O-isopropylidene tartrate.

According to another advantageous embodiment of the process according to the present invention, said process consists in reacting:

a functionalised solid support having the formula:

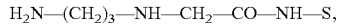

wherein S is as defined previously,
with a dimethyl-2,3-O-isopropylidene tartrate.

The present invention also relates to a support having formula III, as follows:

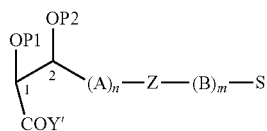

wherein S, B, A, n, m, Z, P1 and P2 are as defined above and Y' represents an organic component.

Preferably, Y' represents a compound or a chain formation of several compounds selected from the group constituted by lipids, nucleotides, said nucleotides being substituted or not, and amino acids, the latter possibly comprising lipids. Generally speaking, Y' thus represents a lipid, an oligonucleotide, a peptide, a pseudopeptide, etc. Y' can comprise one or more types of the aforementioned compounds, Y' then being a homogenous or a heterogenous polymer.

The formula III support can be obtained from the formula I support after chemical modification or derivatisation of the —COX' functional group with the help of a suitable reagent, which will provide a function enabling amino acids, lipids, nucleotides, etc. to be grafted on the support. It is possible, for example, to contemplate grafting a diamine, a dialcohol or an aminoalcohol on the COX' function, with the amine or free alcohol function thus introduced on the support permitting the synthesis of modified peptides.

The formula III support described above can be obtained from the formula I support according to the invention, as described, for example, in "Solid phase organic reactions", Tetrahedron report number 394, Tetrahedron, 1996, 52, 4527-4554 and in "Solid phase organic reactions II", Tetrahedron report number 418, Tetrahedron, 1997, 53, 5643-5678.

The formula III support described above can thus be used to store the synthesised product, said product being separated subsequently from the support, at the time of its use, with simultaneous formation of the α-oxoaldehyde function.

The present invention also relates to a process for the synthesis of organic compounds comprising at least one α-oxoaldehyde function, characterised in that said process is carried out in solid phase and includes the following steps:

preparation of a formula I support as described earlier, said preparation being carried out as described above;

possibly, derivatisation of group X' of said formula I support so as to introduce a function permitting the preparation on the support of organic compound Y' as defined earlier;

preparation of compound Y' in solid phase;

if P1 and P2 are other than a hydrogen atom, deprotection of the two hydroxyl functions in positions 1, 2 protected by P1 and P2 according to formula III as described above;

periodic solid phase oxidation; and isolation of the product formed, functionalised by at least one α-oxoaldehyde function.

Advantageously, the possible step of derivatisation of group X' of the formula I support consists in grafting a diamine, a dialcohol or an aminoalcohol.

As to the possible step of deprotection of the two hydroxyl functions in positions 1, 2 protected by P1 and P2, this is carried out under conditions perfectly familiar to a person skilled in the art and described, for example, in "Protective groups in organic synthesis", Theodora W. Greene and Peter G. M. Wuts, 1991, John Wiley and Sons, Inc., or in "Comprehensive organic synthesis", B. M. Trost and I. Fleming Ed., Pergamon Press, 1991, volumes 1-9.

According to one advantageous embodiment, deprotection of diol-1,2 is carried out in an acid medium, preferably in the presence of trifluoroacetic acid. Deprotection in an acid medium is appropriate, for example and non-limitatively, in the event of P1 and P2 represent acetal, cetal, —SiR'R"R"', tert-butyl, triphenylmethyl, tetrahydropyranyl or methoxymethyl groups.

When the product synthesised using the formula I support according to the invention is a peptide or a protein, this deprotection step also makes it possible, simultaneously, to de-protect the side chains of the amino acids of said peptide or of said protein.

According to another advantageous form of embodiment of the process according to the invention, the deprotection of diol-1,2 (hydroxyl functions in positions 1, 2) takes place in a basic medium. Deprotection in a basic medium is appropriate, for example, when P1 and P2 represent —(CO)R$_1$ ester groups.

The deprotection steps thus yields the product of following formula IV:

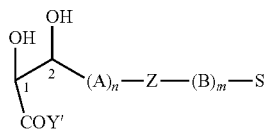

(IV)

Preferably, periodic oxidation is carried out using sodium periodate in a water/acetic acid solvent, such as that described, for example, by L. Zhang et al. in Proc. Natl. Acad. Sci., 1998, 95, 9184-9189. When the product synthesised with the help of the formula I support according to the invention is a peptide or a protein, such a solvent permits the solubilisation of said peptides. The use of such a water/acetic solvent also explains why it is important that the solid support S chosen from formula I of the support according to the invention should have a good solvation property.

However, other mixtures of solvents can be used to carry out the periodic oxidation step. For example, if the formula I support according to the invention is used for the synthesis of peptides containing methionines, periodic oxidation can be carried out in a citrate/methanol/dimethyl sulfide buffer solution; in the case the formula I support according to the invention is used for the synthesis of peptides derivatised by a fatty acid chain, periodic oxidation can be carried out in a tert-butanol/acetic acid/water mixture.

The consequence of the periodic oxidation of the formula IV product is the formation of product Y' functionalised by an α-oxoaldehyde function, as well as the formation of the solid support having the following formula V:

OHC—(A)$_n$—Z—(B)$_m$—S    (V)

in which S, B, A, Z, n and m are as defined above.

In a particularly advantageous manner, the process according to the invention, by virtue of the solid phase oxidation step described above, permits, at the same time, release of the product from the support and formation of the α-oxoaldehyde function at the anchoring point of the product on the support. When the product synthesised on the support is a peptide, the solid phase periodic oxidation step, which is carried out on a deprotected peptide, simultaneously permits the release of the peptide from the support, without it being necessary to carry out an additional homogenous phase deprotection step, and formation of the α-oxoaldehyde function at the anchoring point of of the peptide to the support: this may involve an end of said peptide or a side chain thereof.

The product functionalised by an α-oxoaldehyde thus formed is then isolated, for example by a filtration step followed by purification by high-performance liquid chromatography, by means of techniques known per se.

As to the solid support of formula V represented above, it can advantageously be recycled or regenerated with a view to being re-used, that is to say react with a suitable reagent so as to produce a formula I support according to the invention as described above, as set out in detail below.

The present invention also relates to peptides, characterised in that they comprise at least one α-oxoaldehyde function located in a position other than the N-terminal end of said peptide and not being bound in an amide bond with an amine function located on a side chain of a lysine or an ornithine, and in that they are obtained according to the process described above.

Such peptides can advantageously be used in chemical ligation reactions.

The present invention also relates to a method of synthesis of a library of organic compounds, characterised in that it includes:

supplying a plurality of solid support surfaces having the formula S—(B)$_m$—Y, wherein B, S, Y and m are as described above;

reacting them with a compound selected from the group constituted by the cyclic anhydrides of tartaric acid or of one of its derivatives and the compounds of formula II

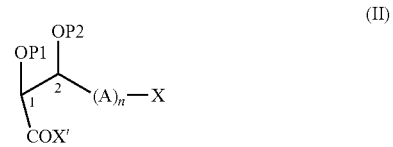

(II)

wherein n, A, P1, P2, X' and X are as defined above, so as to obtain a support that can be used for the synthesis of compounds comprising an α-oxoaldehyde function;

reacting the support obtained with mixtures of organic molecules, as described earlier in connection with the obtaining of a formula III support from a formula I support; and obtaining a library of organic compounds.

Said organic molecules are reacted with the support described above for example as described in "The combinatorial index", 1998, Academic Press, London.

Said organic molecules can be, among others, amino acids, nucleotides or lipids; the organic compounds obtained are then peptides, oligonucleotides or lipids.

The present invention also relates to a library of organic compounds, characterised in that it is obtained according to the process described above.

The organic compounds of this library of compounds can be separated from the insoluble support in order to be used subsequently, as described above in connection with the process for the synthesis of organic compounds comprising an α-oxoaldehyde function.

The present invention also relates to the use of a compound selected from the group constituted by the cyclic anhydrides of tartaric acid or of one of its derivatives and the compounds of formula II:

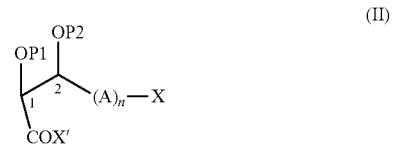

(II)

wherein n, A, P1, P2 and X' and X are as defined above, for the derivatisation of a solid support at least the surface of which has the property of being well solvated in an aqueous or partially aqueous medium, the resulting support being usable for the synthesis, in solid phase, of compounds comprising at least one α-oxoaldehyde function.

Preferably, said solid support at least the surface of which has the property of being well solvated in an aqueous or partially aqueous medium corresponds to the formula S—(B)$_m$—Y, S, B, m and Y being as defined earlier.

The cyclic anhydride of tartaric acid or of one of its derivatives is advantageously the di-O-benzoyl-tartaric anhydride or the diacetyl-tartaric anhydride.

The formula II compound is advantageously such that group A includes a carbonyl group in alpha position of the —OP2 group and represents tartaric acid or a derivative of tartaric acid.

Alternatively, the formula II compound is selected from the family including mucic acid, saccharic acid, glucaric acid, their salts and their derivatives.

A further object of the present invention is a process for preparing a diagnostic reagent on a solid support, characterised in that it comprises the following steps:
- ligation of organic compounds comprising at least one α-oxoaldehyde function, obtained using the above-described process, to a suitably functionalised microtitration plate,
- obtaining a microtitration plate on which said organic components are covalently fixed.

The reagent obtained can be used to develop immunological reagents or pharmacological tests.

Said organic compounds are preferably peptides, oligonucleotides or lipids.

Said microtitration plate is advantageously functionalised so as to permit the ligation of said organic compounds with an oxime, oxazolidine or hydrazone bond.

Another object of the present invention is a process for obtaining a biochip, characterised in that it includes a step of grafting oligonucleotides comprising at least one α-oxoaldehyde function, obtained using the process described above, onto a solid support.

In the biochips thus obtained, the oligonucleotides are fixed covalently to the solid support.

These biochips make it possible, in particular, to follow up the expression of genes according to the concept presented in Science, 1995, 270, 467-470.

According to one advantageous embodiment of the process according to the invention, said solid support is a surface made of glass or silicon.

According to another advantageous form of embodiment of the process according to the invention, said biochip is an ADN chip.

BRIEF DESCRIPTION OF THE DRAWINGS

In addition to the aforementioned arrangements, the invention includes yet other arrangements which will emerge from the description that follows, which refers to examples of supports according to the invention and to examples of processing of the α-oxoaldehyde synthesis process according to the present invention, as well as to the annexed figures, wherein.

In addition to the aforementioned arrangements, the invention includes yet other arrangements which will emerge from the description that follows, which refers to examples of supports according to the invention and to exemples of processing of the α-oxoaldehyde synthesis process according to the present invention, as well as to the annexed figures, wherein.

It is to be clearly understood, however, that these examples are given solely by way of illustration of the object of the invention, of which they in no way constitute a limitation.

EXAMPLE 1

Figure 1:
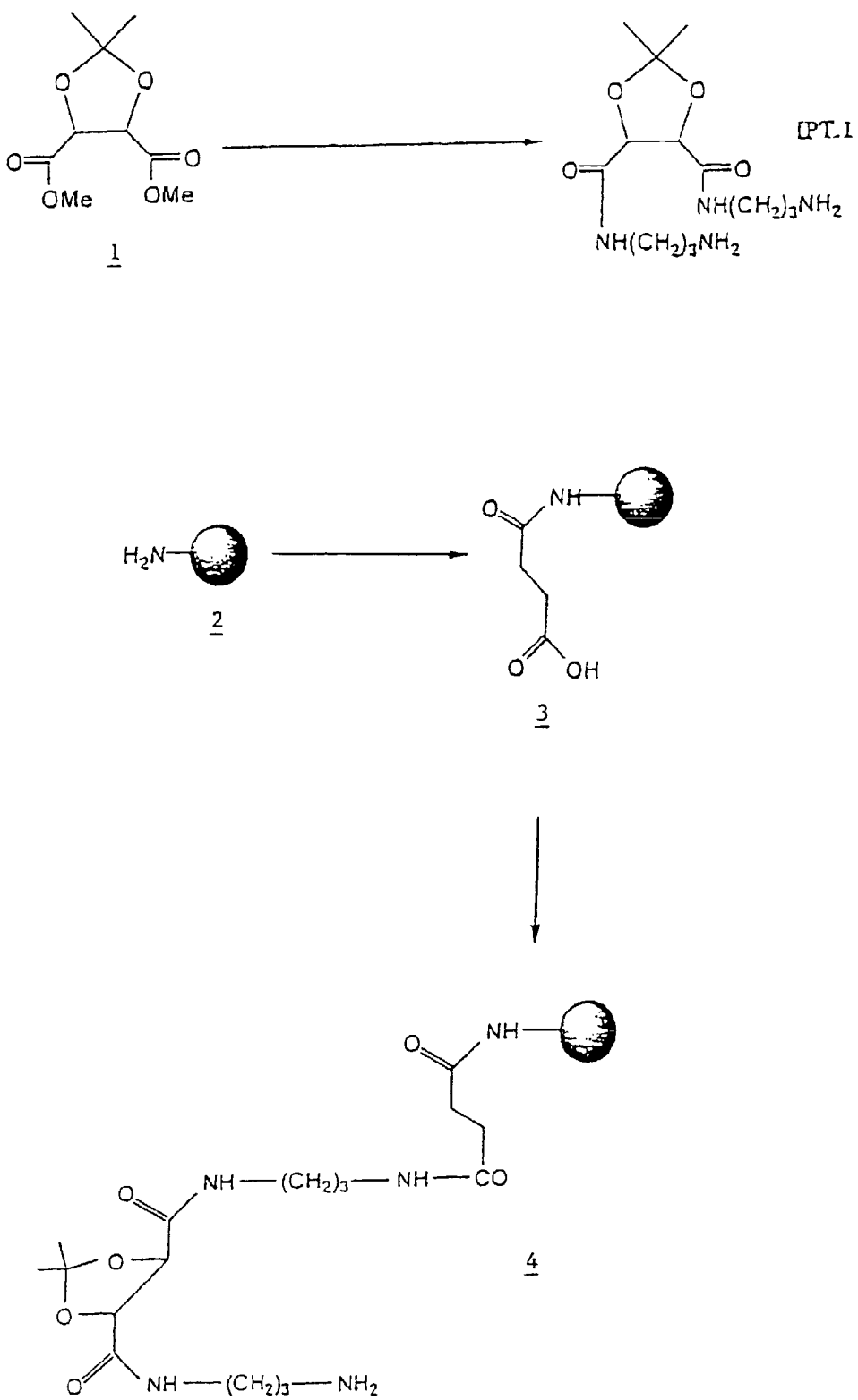
FIGS. 1 and 2 represent the steps of synthesis of formula I supports according to the invention.

Synthesis of a Formula I Support According to the Invention from an Amino-PEGA® Resin and (+)-dimethyl-2,3-O-isopropylidene-D-tartrate The different steps in this synthesis are summarised in FIG. 1.

2 ml (9.16 mmol) of (+)-dimethyl-2,3-O-isopropylidene-D-tartrate (supplied by ACROS) 1, hereinafter referred to as IPT, are added, for 45 minutes, to 10 ml (120 mmol) of 1,3-diaminopropane. After stirring for 5 h 30 at room temperature, the excess 1,3-diaminopropane is eliminated by evaporation under reduced pressure in order to isolate the compound IPT-1, the nuclear magnetic resonance and infrared analysis of which is as follows:

RMN $^1$H 300 MHz (DMSO-$d_6$, TMS): 8.19 (t, 2H, J=5.5 Hz, CONH), 4.46 (s, 2H, COCH), 3.15 (m, 4H, CH$_2$NHCO), 2.50 (m, 4H, CH$_2$NH$_2$), 1.48 (q, 4H, J=6.6 Hz, NHCH$_2$CH$_2$), 1.39 (s, 6H, (CH$_3$)$_2$C). RMN $^{13}$C 75 MHz (DMSO-$d_6$, TMS): 171.5, 111.5, 77.6, 39.0, 36.4, 32.6, 26.2. IR (cm$^{-1}$): 3356.8, 2940.3, 1660.7, 1537.6, 1084.6.

Elemental analysis of the compound IPT-1 is as follows: C: 49.67%, H: 9.14%, N: 18.08%, O: 22.84%.

Analysis of compound IPT-I using electrospray mass spectrometry yields a value of 302.2, corresponding to the mass of this compound.

The protocol continues as follows: 0.4 mmol of amino-PEGA® resin 2 (0.4 mmol/g, Novabiochem) are soaked in a minimum volume (9.6 ml) of dimethylformamide (DMF), and then 400.3 mg (4.0 mmol) of succinic anhydride are added, in the presence of 697 µl (4.0 mmol), of diisopropylethylamine (DIEA) and of 2 ml of DMF. The resulting support 3 is washed with DMF (twice 2 minutes), dichloromethane (twice 2 minutes and NMP (twice 2 minutes).

1209 mg (40 mmol) of compound IPT-I dissolved in 1 ml of NMP are added to support 3 previously obtained, soaked with a minimum volume of NMP. 265.4 mg (0.6 mmol) of benzotriazol-1-yl-oxy-tris (dimethylamino)-phosphonium hexafluorophosphate (BOP) are then added in a single step, and the mixture is stirred for 1 h. The resulting support 4 is washed with DMF (4 times 2 minutes), dichloromethane (twice 2 minutes) and ether (twice 2 minutes), and then vacuum dried.

There is thus obtained a formula I support according to the invention, wherein S is an amino-PEGA® resin, m and n represent 1, B is a —$(CH_2)_2$—CO—NH chain, Z is an amide functional group, A is a —CO—NH—$(CH_2)_3$— chain, P1 and P2 form together an isopropylidine protective group, and X' represents a —NH—$(CH_2)_3$—$NH_2$ chain.

This support is obtained by reaction of an S—$(B)_m$—Y support with a formula II compound, as defined earlier, with Y=—COOH and X=—$NH_2$ (in formula II).

EXAMPLE 2

Figure 2:
Figure 2:
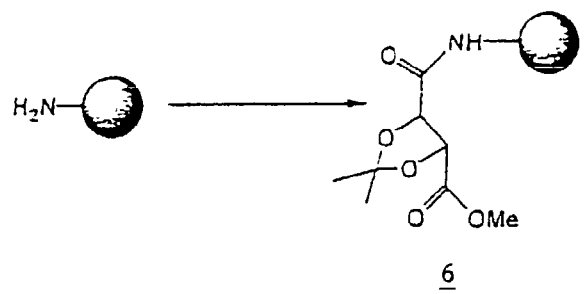
Figure 2:
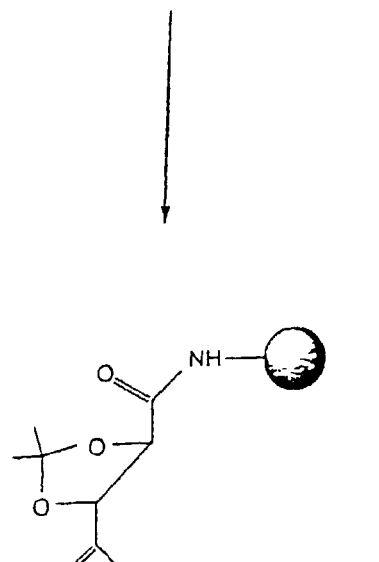

Synthesis of Another Formula I Support According to the Invention from an Amino-PEGA® Resin and (+)-dimethyl-2,3-O-isopropylidene-D-tartrate The different steps in this synthesis are summarised in FIG. 2.

7.2 μl (0.4 mmol) of water are added to 873 μl of (+)-dimethyl-2,3-O-isopropylidene-D-tartrate (supplied by ACROS) at room temperature. 59.8 μl (0.4 mmol) of 1,8-diaza-bicyclo [5.4.0] undec-7-ene (DBU) are then added to this solution, and the resulting mixture is stirred for 1 h. Mixture 5 is obtained.

0.1 mmol of amino-PEGA® resin (0.4 mmol/g, Novabiochem) are washed with 5% DIEA in dichloromethane and DMF. The resin is soaked with a minimum volume of DMF, and then mixture 5 is added thereto, as well as 177 mg (0.4 mmol) of BOP reagent (an electrophilic activating agent of the carboxylate function generated in compound 5) dissolved in 1 ml of DMF. After stirring for 40 minutes, the resulting support 6 is washed with DMF (4 times 2 minutes), and dichloromethane (twice 2 minutes).

There is thus obtained a formula I support according to the invention, wherein S is an amino-PEGA® resin, m and n represent O, Z is an amide functional group, P1 and P2 together form an isopropylidene protective group and X' represents a methoxy group. It is obtained by reaction of an S—$(B)_m$—Y support with a formula II compound as defined earlier, with Y=—$NH_2$ and X=—$COO^-$ transformed by an electrophilic activating agent (BOP).

A diamine can advantageously be grafted on the —COX' functional group in order to introduce on the support a free amine function permitting the synthesis of modified peptides.

For this purpose, support 6 is soaked in a minimum volume of DMF, and 1.0 g (7.7 mmol) of 1,7-diaminoheptane dissolved in 1 ml of DMF are added thereto. After stirring for 1 h, the resulting support 7 is washed with DMF (5 times 2 minutes), with dichloromethane (twice 2 minutes) and ether (twice 2 minutes), and then vacuum dried.

EXAMPLE 3

Synthesis of Two Other Formula I Supports According to the Invention from Aminomethyl-NOVAGEL® and ARGOGEL®-$NH_2$ Resins and (+)-dimethyl-2,3-O-isopropylidene-D-tartrate The protocol used is similar to the one described in Example 2.

The aminomethyl-NOVAGEL® (0.76 nmol/g) and ARGOGEL®-$NH_2$ (0.41 mmol/g) resins, marketed by Novabiochem in the case of the first resin, and by Argonaut Technologies in that of the second, are neutralised with a solution of 5% DIEA in $CH_2Cl_2$, and then swollen in a minimum volume of DMF.

4.8 mmol of DBU (717.8 μl) are added in a single step to a solution containing 48 mmol of (+)-dimethyl-2,3-O-isopropylidene-D-tartrate (10.47 ml) and 4.8 mmol of water (86.4 μl). After stirring for one hour, one half of this solution is poured onto 0.6 mmol of aminomethyl-NOVAGEL® resin (0.76 mmol/g), and the other half over 0.6 mmol of ARGOGEL®-$NH_2$ resin (0.41 mmol/g).

In the case of each resin, 1.06 g (2.4 mmol) of BOP dissolved in 6 ml of DMF for the first coupling (45 minutes) and 12 ml for the second (45 minutes) are added in a single step. The resins were then washed with DMF (4 times 2 minutes) and $CH_2Cl_2$ (twice 2 minutes), and then treated with $Ac_2O$/DIEA/$CH_2Cl_2$ (10%/5%/85%) for 10 minutes.

There are thus obtained formula I supports according to the invention in which S is a NOVAGEL® resin or an ARGOGEL® resin, m and n represent O, Z is an amide functional group, P1 and P2 together form an isopropylidene protective group and X' represents a methoxy group.

As described in Example 2, a diamine can advantageously be grafted on the —COX' group of the support. For this purpose, a solution of 1.3-diaminopropane, 7.70 M in DMF (3 ml) is added to the supports. After stirring for 1 hour, the supports are washed with DMF (5 times 2 minutes), $CH_2Cl_2$ (twice 2 minutes) and then ether (twice 2 minutes) before being dried at reduced pressure. The charge of the supports is determined by analysing, by UV spectrometry, the fulvene-piperidine adduct released after coupling of the Fmoc-Gly-OH and deprotection with 20% piperidine in DMF. The charge is thus 0.34 mmol/g in the case of the aminomethyl-NOVAGEL® resin based support according to the invention, and 0.23 mmol/g in the case of the ARGOGEL®-$NH_2$ resin based support according to the invention.

EXAMPLE 4

Figure 3:
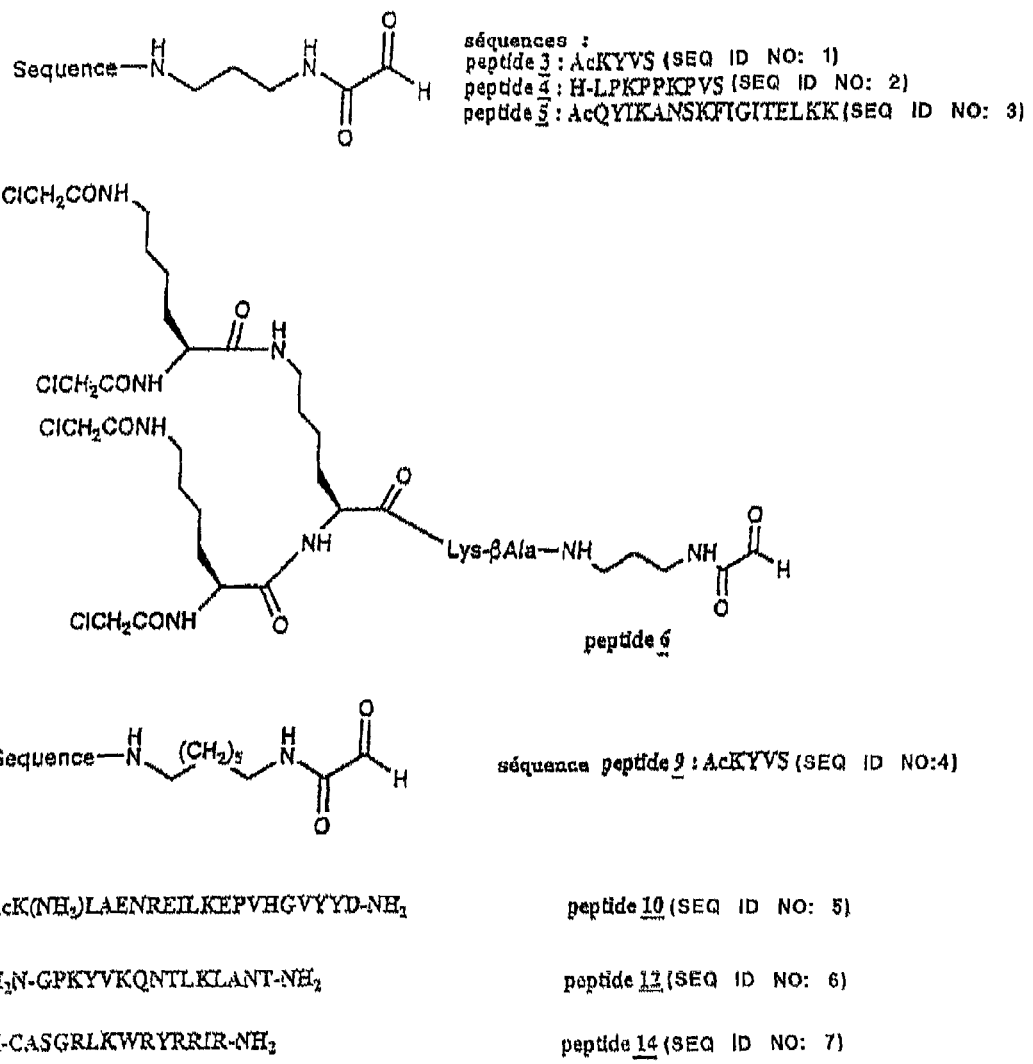
FIG. 3 represents the peptides 3-6 (SEQ ID NOS: 1-3, respectively) and 9 (SEQ ID NO: 4) synthesised using the supports according to the invention, as well as the peptides 10, 12 and 14 (SEQ ID NOS: 5-7, respectively) synthesised using conventional solid phase techniques.

Synthesis of Peptides Bearing an α-oxoaldehyde Function at Their C-terminal End Using the Supports According to the Invention Peptides 3-6 and 9 synthesised using the supports according to the invention are shown in FIG. 3.

a) Solid Phase Peptide Synthesis

Peptides 3-5 and 9 were synthesised using support 4 described in example 1 and support 6 described in example 2 (0.2 mmol/g), respectively.

Peptide synthesis was carried out in automated fashion by means of a 431A synthesiser supplied by Applied Biosystem, according to the methodology described by Fields, G. B. et al. in Int. J. Pept. Protein, 1990, 35, 161.

The amino acids protected by Fmoc (9-fluorenylmethoxycarbonyl) were supplied by the Propeptide company (Vert-Le-Petit, France). The side chain protective functional groups are as follows: Arg(2,2,5,7,8-pentamethylchroman-6-sulfonyl), Asn (trityl), Asp (tert-butyl), Gln (trityl), Lys (tert-butyloxycarbonyl, also referred to as Boc), Ser (tert-butyl), Thr (tert-butyl), Tyr (tert-butyl).

The syntheses were carried out from 0.1 mmol of support, 10 activated amino acid equivalents having been used for each coupling step. A single coupling was used for peptides 3 and 9. In the case of the other peptides, the amino acids were coupled twice.

Following each coupling or double coupling, a residual amine function capping is carried out in order to prevent the formation of deleted peptides, before resuming the synthesis.

For this purpose, the amine functions are blocked with an acetyl group by reaction with an Ac$_2$O/DIEA/N-methyl-pyrrolidone (NMP) mixture, 4.75/2.25/91.5 (by volume) containing 7.5 mM of N-hydroxybenzotriazole (HOBt).

When the peptidic synthesis is completed, if necessary (peptides 3, 5 and 9, which comprise acetylated amine functions at their ends), the end of the peptide is acetylated by reaction with the mixture described above.

Peptide 6 was synthesised manually from 0.1 mmole of the support 4 described in example 1 (0.2 mmol/g) using 10 equivalents of activated amino acid for each coupling step. The amino acids were activated by a mixture, in DMF, of HBTU/HOBt/DIEA (10 eq./10 eq./30 eq.) (HBTU: N-[(1H-benzotriazol-1-yl) (dimethylamino)-methylene]-N-methyl-methanaminium N-oxide hexafluorophosphate; HOBt: N-hydroxybenzotriazole; DIEA: diisopropylethyl-amine). The amine functions that have not reacted at the time of the coupling step are then blocked with an acetyl group (reaction with an 10/5/85 Ac$_2$O/DIEA/CH$_2$Cl$_2$ mixture by volume). Single couplings (1 h) were carried out in the case of the Fmoc-βAla-OH and the Fmoc-L-Lys (Boc)-OH. The Fmoc-L-Lys (Fmoc)-OH was linked twice. Chloroacetic acid (2 equivalents) was linked twice using activation with diisopropylcarbodiimide (2 equivalents) in DMF for 30 minutes.

b) Deprotection and Cleavage from the Support

Deprotection of the peptides synthesised in solid phase, as described above, is carried out in solid phase using:

in the case of the peptides 3, 4, 6 and 9: 10 ml of a trifluoroacetic acid/water/anisole mixture (95/2.5/2.5 by volume) for 2 h at room temperature.

in the case of peptide 5: 10 ml of trifluoroacetic acid/water/triisopropylsilane mixture (95/2.5/2.5 by volume) for 3 h at room temperature.

The supports are then washed with dichloromethane (4 times 2 minutes) and ether (twice 2 minutes), and then dried at reduced pressure.

This deprotection step allows both the deprotection of the amino acid side chains of the peptides and that of the neighbouring hydroxyl functional groups (in positions 1 and 2) of formula III support according to the invention, so as to form the formula IV according to the invention (elimination of the P1 and P2 protective functional groups).

c) Solid Phase Periodic Oxidation 0.1 mmole of the support on which the de-protected peptide is bound, in dry form (step b) above), are soaked with 5 ml of a water/acetic acid mixture (2/1 by volume) for 15 minutes. 128.3 mg (6 equivalents) of sodium periodate dissolved in 2 ml of a water/acetic acid mixture (5/1 by volume) are then added in a single step. This step simultaneously allows the formation of the C-terminal α-oxoaldehyde function and cleavage of the peptide from the support.

After stirring for 2 minutes, the support is filtered and washed twice with 6 ml of water, for 1 minute. This solution is then poured into 200 μl of ethyleneglycol and injected onto a reverse phase high-performance liquid chromatography (RP-HPLC) column of the Hyperprep C18 type marketed by Interchim (Monlucon, France). The peptides are purified using a linear gradient of a water/acetonitrile eluent containing 0.05% of trifluoroacetic acid.

The peptides 3, 4, 6 and 9 were directly freeze dried. Their respective yields after purification by RP-HPLC are 38.0%, 26.0%, 30.1% and 32.9%.

As to peptide 5, 500 mg of (+)-D-mannitol (supplied by Sigma) are added to it before freeze drying it, the purpose of this being to avoid peptide aggregation phenomena.

The peptide 5 content (3.3%) was determined by quantitative analysis of the amino acids using detection with ninhydrine after total acid hydrolysis using a 10/1 HCl 6N/phenol mixture at 110° C. for 24 h. The peptide 5 yield is 6.1%.

EXAMPLE 5

Synthesis of a Peptide Functionalised in C-terminal Position with an α-oxoaldehyde, said Peptide Containing Methionines The following peptide:

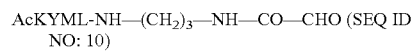

AcKYML-NH—(CH$_2$)$_3$—NH—CO—CHO (SEQ ID NO: 10)

was prepared in solid phase using support 4 described in Example 1, according to the protocol described in example 4. The protective functional groups of the amino acid side chains are, respectively, the Boc group in the case of lysine and the O-tert-butyl group in that of tyrosine.

The deprotection step is carried out in solid phase using 10 ml of a trifluoroacetic acid/water/ethanedithiol (EDT)/triisopropylsilane mixture (94/2.5/2.5/1 by volume) for 2 h at room temperature.

The support is then washed with dichloromethane and ether, as described in Example 4, and then vacuum dried prior to the periodic oxidation step.

Owing to the presence of methionines, periodic oxidation of the peptide necessitates special conditions suitable for preventing oxidation of this amino acid (risk of formation of methionine sulfoxide): use of a pH close to neutral and of dimethyl sulfide, which performs a protective role, being oxidised in preference to methionine.

For the purpose of periodic oxidation and cleavage of the peptide from the support, 270 mg of dry support are thus placed in a reactor. To it are added 5.4 ml of sodium citrate buffer (pH 6), 5.4 ml of methanol and 0.9 ml of Me$_2$S (dimethyl sulfide).

15 minutes later, 63.18 mg (6 equivalents) of sodium periodate are added in 2 ml of citrate buffer in a single step. After stirring for 15 minutes, the same quantity of sodium periodate is again added. After stirring for 15 minutes, the supernatent is added quickly to 0.36 of ethylene glycol.

The support is immediately reconditioned in 5.4 ml of citrate buffer at pH 6.0, 5.4 ml of methanol and 0.9 ml of Me$_2$S to be treated in the same way with sodium periodate. This protocol is repeated 10 times.

The peptide is isolated with a yield of 15.3% after purification by RP-HPLC.

EXAMPLE 6

Figure 4:
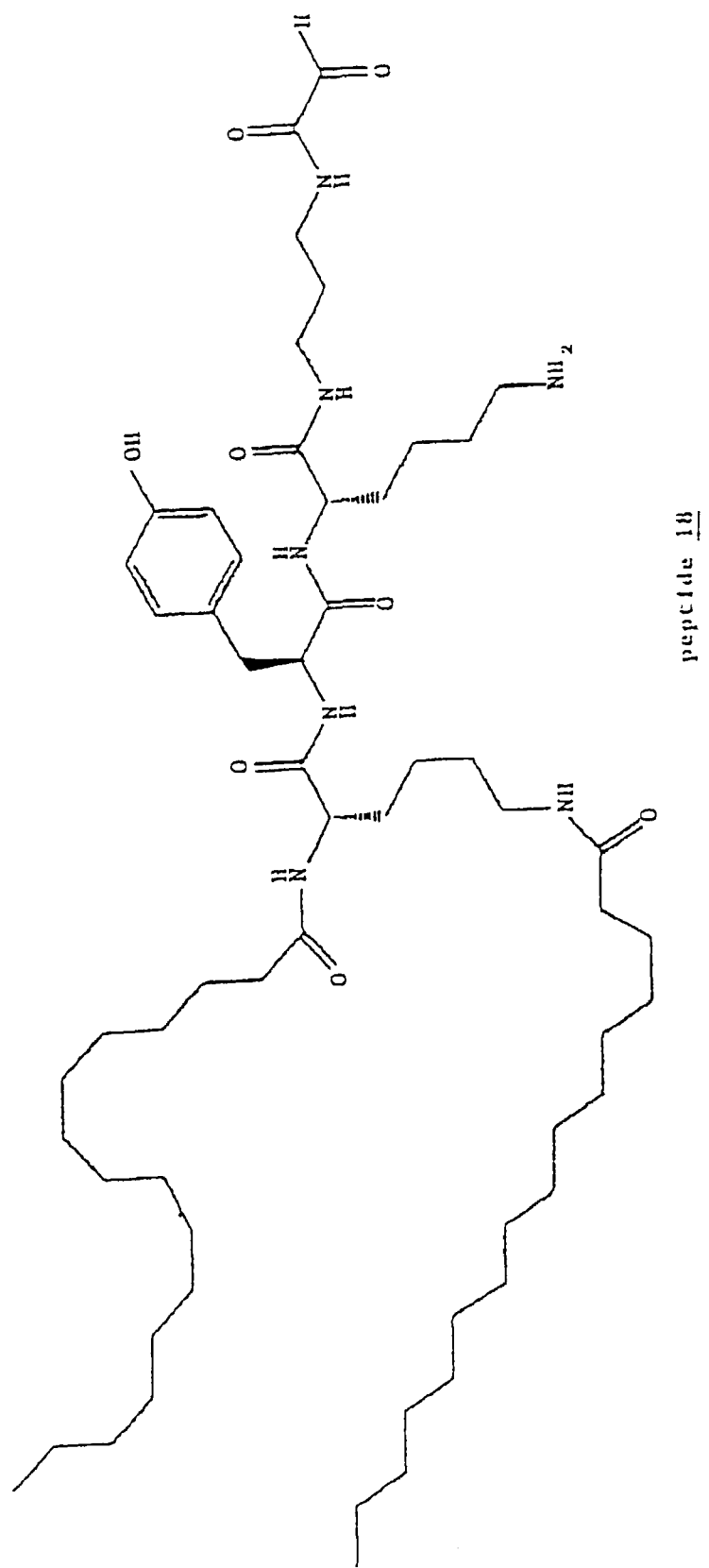
FIG. 4 represents peptide 18, namely a peptide modified by fatty acids and comprising an α-oxoaldehyde function, said peptide being synthesised using a support according to the invention.

Synthesis of Peptide 18 (FIG. 4) Functionalised in C-terminal Position by an α-oxoaldehyde, said Peptide Being Modified by Fatty Acids Peptide synthesis is carried out using the support of formula 4 according to the invention, obtained as described in example 1. Use is made of 410 mg of support 4 (0.2 mmol/g, or 0.082 mmol) swollen in DMF by three successive washing operations of 2 minutes each. Unless otherwise specified, all the reactions take place at room temperature.

Introduction of a First Lysine 76.8 mg of Fmoc-Lys(Boc)-OH (0.164 mmol, or 2 equivalents), 25.1 mg of HOBt (0.164 mmol, or 2 equivalents) and 62.2 mg of HBTU (0.164 mmol, or 2 equivalents) are introduced into a tube and dissolved in 1 ml of DMF. Thereto are added 115 μl of DIEA (0.656 mol, or 8 equivalents). After stirring for 1 minute, the activated solution obtained is placed on support 4. After stirring for 1 h, the support is rinsed 3 times 2 minutes with DMF, and then 3 times 2 minutes with dichloromethane. Disappearance of the reactive amine is evaluated using the qualitative Kaiser test (Anal. Biochem., 1970, 34, 595) (negative) and the TNBS test (*Anal. Biochem.*, 1976, 71, 260-264) (negative).

Once the reactive amine has been eliminated, the support is rinsed 3 times 2 minutes with NMP. The Fmoc functional group is de-protected by addition of a large excess amount of 20% piperidine in NMP. The support is then rinsed 3 times 2 minutes with NMP and 3 times 2 minutes with $CH_2Cl_2$. The quality of deprotection is evaluated using the qualitative Kaiser test (positive).

Introduction of a Tyrosine

The support is rinsed 3 times 2 minutes with DMF. 75.4 mg of Fmoc-Tyr(tert-butyl)-OH (0.164 mmol, or 2 equivalents), 25.1 mg of HOBt (0.164 mmol, or 2 equivalents) and 62.2 mg of HBTU (0.164 mmol, or 2 equivalents) are introduced into a tube and dissolved in 1 ml of DMF. One then proceeds in the same way as described above as regards the introduction of a lysine.

Introduction of Another Lysine

The support is rinsed 3 times 2 minutes with DMF. 96.9 mg of Fmoc-Lys(Fmoc)-OH (0.164 mmol, or 2 equivalents), 25.1 mg of HOBt (0.164 mmol, or 2 equivalents) and 62.2 mg of HBTU (0.164 mmol, or 2 equivalents) are introduced into a tube and dissolved in 1 ml of DMF. One then proceeds in the same way as described above as regards introduction of the first lysine.

Modification of the Peptide by Fatty Acids

The support on which the tri-peptide Lys-Tyr-Lys has been synthesised is washed 3 times 2 minutes with a $DMF/CH_2Cl_2$ mixture (50/50 by volume). 84.1 mg of palmitic acid (0.328 mmol, or 4 equivalents) are introduced into a tube and dissolved in 500 µl of the 50/50 $DMF/CH_2Cl_2$ mixture. 50.2 mg of HOBt (0.328 mmol, or 4 equivalents) and 124.4 mg of HBTU (0.328 mmol, or 4 equivalents) are introduced into the same tube and dissolved in 1 ml of 50/50 $DMF/CH_2Cl_2$. The contents of the two tubes are mixed, stirred for 1 minute, and then 230 µl of DIEA (1.312 mmol, or 16 equivalents) are added thereto. After stirring for 1 minute, the activated solution obtained is placed on the support. After stirring for 1 h, the support is washed 3 times 2 minutes with the 50/50 $DMF/CH_2Cl_2$ mixture.

Into the same tube are introduced once again 84.1 mg of palmitic acid (0.328 mmol, or 4 equivalents) and 146 mg of PyBrop (bromo-tris-pyrrolidino-phosphonium hexafluorophosphate) (0.328 mmol, or 4 equivalents) dissolved in 1 ml of 50/50 $DMF/CH_2Cl_2$. 173.5 µl of DIEA (0.984 mmol, or 12 equivalents) are solubilised in 1 ml of 50/50 $DFM/CH_2Cl_2$. The two solutions are mixed for 1 minute. The resulting solution is placed on the support. After stirring for 1 h, the support is washed 3 times 2 minutes with the 50/50 $DFM/CH_2Cl_2$ mixture, and then 3 times 2 minutes with $CH_2Cl_2$. Disappearance of the reactive amine is evaluated using the TNBS test (negative).

Obtaining Peptide 18

The support resulting from the operations previously described is vacuum dried overnight. 20 ml of a trifluoroacetic acid, water and triisopropylsilane mixture (95/2.5/2.5 by volume) is placted on the support. Stirring is carried out for 2 minutes, and then the trifluoroacetic acid/water/triisopropylsilane mixture is eliminated and 20 ml of this mixture is re-placed on the support. After stirring for 20 minutes, the support is washed 3 times 2 mihutes with $CH_2Cl_2$. The support is vacuum dried overnight.

112 mg of dry support (0.224 mmol) are washed twice 2 minutes with tert-butanol. 28.9 mg of sodium periodate (0.135 mmol, or 6 equivalents) are dissolved in 200 µl of water. Thereto are added 200 µl of a 33% acetic acid solution in water and 200 µl of tert-butanol. The resulting solution is placed on the support.

After stirring for 15 minutes, the solution, having been deposited on the support, is introduced into a tube containing 80 µl of ethylene glycol. The support is washed with 600 µl of a 33% water/acetic acid mixture in water/tert-butanol (1/1/1 by volume). The resulting solution is also introduced into the tube containing the ethylene glycol. Peptide 18 (FIG. 4) precipitates in the tube. Its precipitation is favoured by placing the tube at −20° C. The precipitate is washed with 200 µl of a 33% water/acetic acid mixture in water/tert-butanol (1/1/1 by volume). The resulting solution is replaced at −20° C. to cause the product to precipitate, and is then centrifuged. The pellet thus recovered represents 50% of the total product formed on the support. The rest of the product is extracted after the support has been washed 6 times with 4 ml of a tert-butanol/methanol mixture at 50° C., followed by cold precipitation in the extraction mixture. The total extraction yield is 79%. Using 112 mg of support (0.224 mmol), 20.1 mg of pure product 18 were isolated. $[M+Na]^+$ calculated: 1048; found: 1048.

EXAMPLE 7

Figure 5:
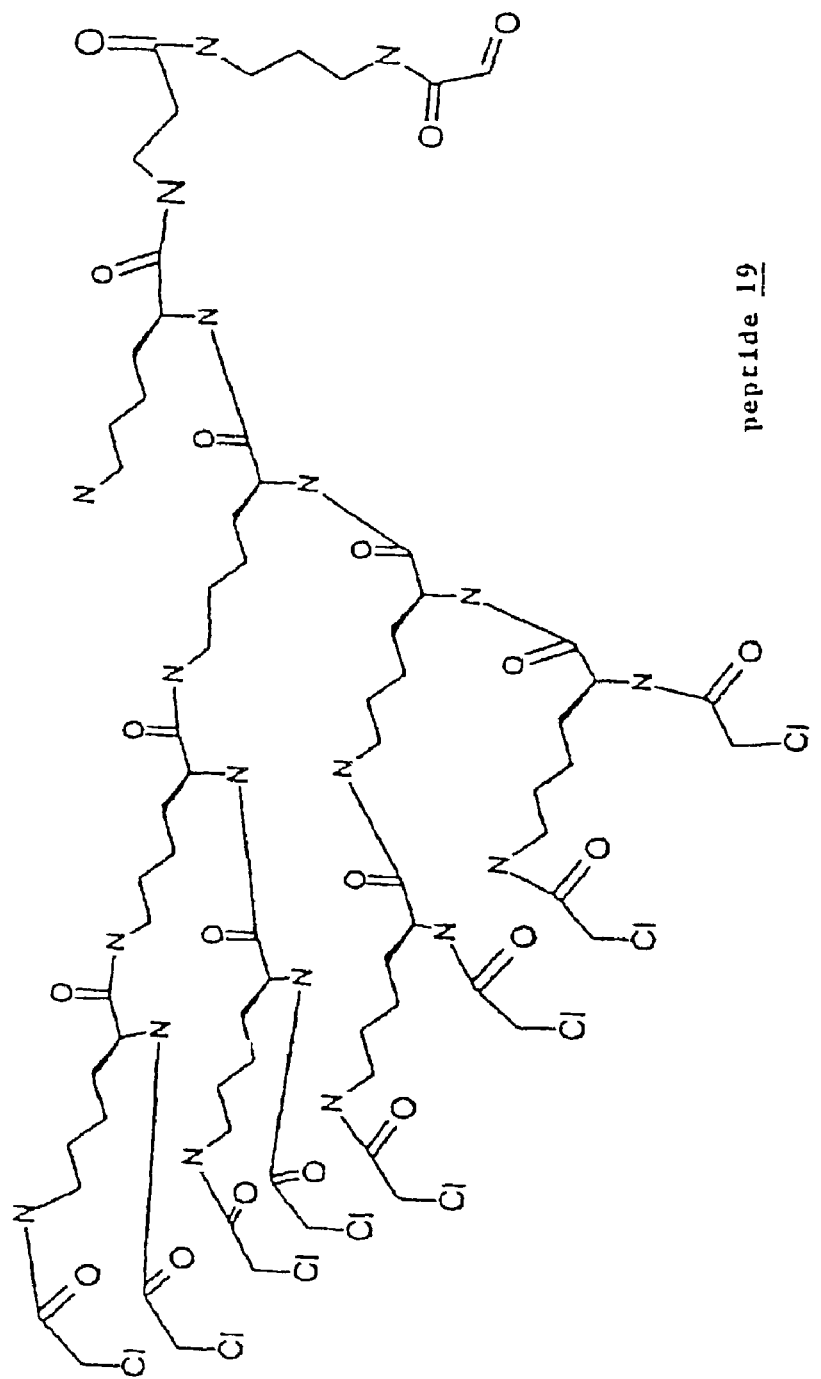
FIG. 5 represents peptide 19, namely a peptide of the poly-lysine type functionalised by 8 chloroacetyl functions and by an α-oxoaldehyde function, said peptide being synthesised using a support according to the invention.

Synthesis of Peptide 19 with a Valency of 8 (FIG. 5), Namely a Peptide of the Poly-lysine Type Functionalised by 8 Chloroacetyl Functions and by an α-oxoaldehyde Function, said Peptide Being Synthesised Using a Support According to the Invention Peptide 19 is synthesised manually from 0.1 mmol of support 4 (0.2 mmol/g) obtained in accordance with example 1. All the amino acids (10 equivalents per free —$NH_2$ function of the support) are activated with HBTU/HOBt/DIEA (10 equivalents/10 equivalents/30 equivalents) in DMF. The peptides are acetylated with $Ac_2O/DIEA/CH_2Cl_2$ (dichloromethane) mixture: 10/5/85 (by volume) after each coupling step. Single couplings (1 h) are carried out in the case of Fmoc-βAla-OH and Fmoc-L-Lys(Boc)-OH. The Fmoc-L-Lys (Fmoc)-OH are all linked twice (1 h). The chloroacetic acid (64 equivalents) is linked twice with one activation with diisopropylcarbodiimide (32 equivalents).

The functionalised peptide is de-protected in solid phase using 10 ml of $TFA/H_2O$/anisole (95/2.5/2.5 by volume) for 2 hours at room temperature. The support is then washed with $CH_2Cl_2$ (4 times 2 minutes) and ether (twice 2 minutes), and dried at reduced pressure.

Periodic oxidation is carried out after swelling the support (0.1 mmol) with 5 ml of water/acetic acid (2/1 by volume) for 15 minutes, using 128.33 mg of sodium periodate dissolved in 2 ml of water/acetic acid (5/1 by volume) and added in a single step to the support. The suspension is stirred for 2 minutes, and then the support is filtered and washed with 6 ml of water (2×1 minute). The filtrates are pooled and 200 µl of ethylene glycol are added in order to stop the oxidation reaction.

The product is purified by RP-HPLC on a C18 Hyperprep column (15×300 mm). The product is purified with a 0-50% linear gradient of eluent B for 100 minutes, at the rate of 3 ml/minute and with absorbance measurement at 215 nm.

Eluent A: water containing 0.05% by volume of TFA.
Eluent B: acetonitrile/water (4/1 by volume) containing 0.05% of TFA.

The pure fractions are directly collected and freeze dried. 45 mg of purified peptide 19 are obtained, i.e. a yield of 23.5%.

EXAMPLE 8

Figure 6:
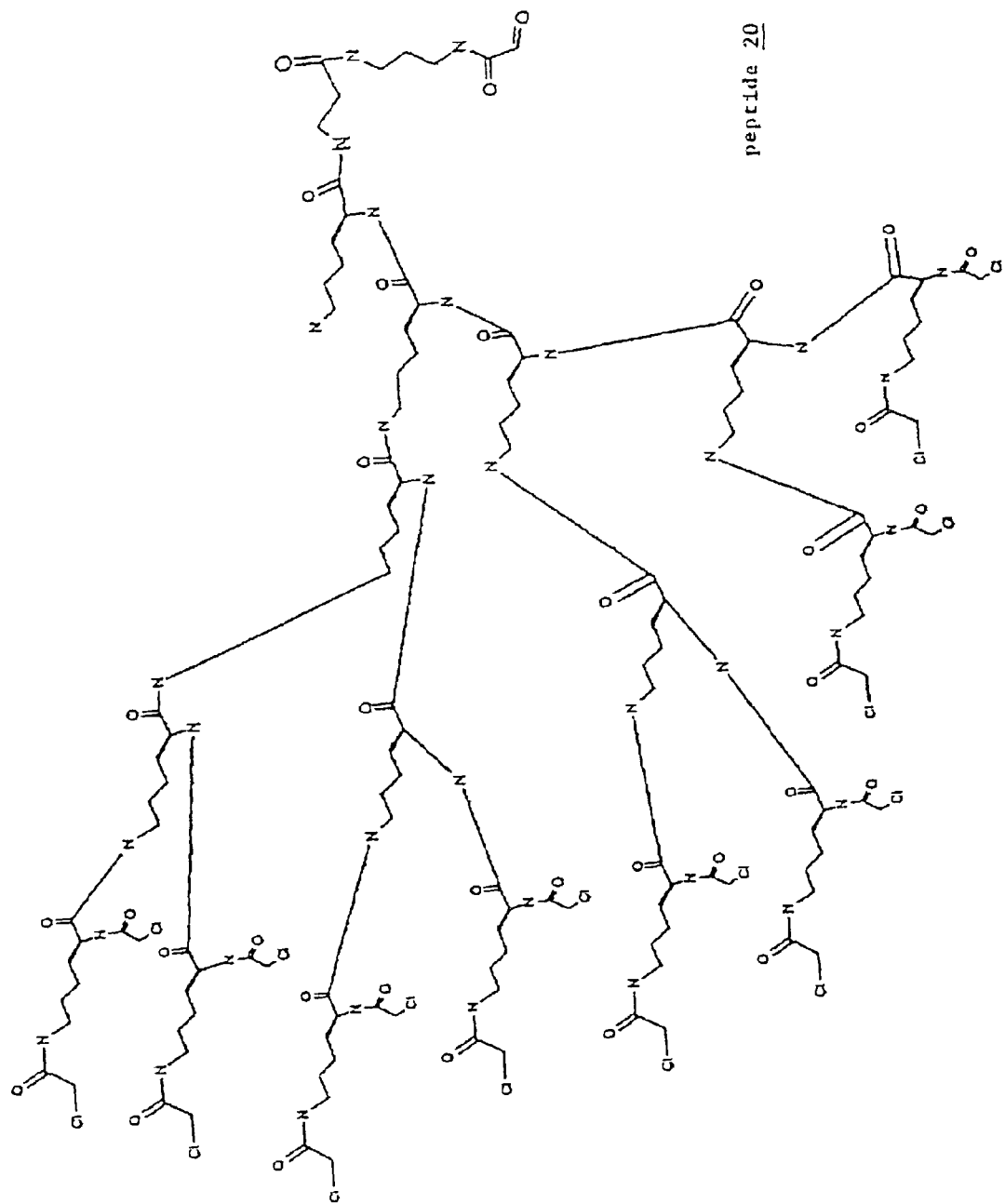
FIG. 6 represents peptide 20, namely a peptide of the poly-lysine type functionalised by 16 chloroacetyl functions and by an α-oxoaldehyde function, said peptide being synthesised using a support according to the invention.

Synthesis of Peptide 20 with a Valency of 16 (FIG. 6), Namely a Peptide of the Poly-lysine Type Functionalised with 16 Chloroacetyl Functions and with an Oxoaldehyde Function, said Peptide Being Synthesised Using a Support According to the Invention The peptide 20 is synthesised from 0.1 mmol of support 6 (0.2 mmol/g) obtained in accordance with Example 2 and functionalised with a diamine according to the protocol described in Example 2, the diamine used being 1,3-diaminopropane.

The activation reagents used during the coupling of the amino acids are HBTU, HOBt and DIEA, whereof the number of equivalents used per —$NH_2$ function at the time of each coupling will be given below.

The duration of activation is one minute prior to introduction on the support. Deprotection of the Fmoc groups is carried out with 20% piperidine in NMP (once for 5 minutes and once for 20 minutes). A Kaiser test and a TNBS test are conducted after each coupling step in order to check for the absence of reactive —$NH_2$ functions.

The first coupling is carried out with 10 equivalents of Fmoc-β-Ala-OH/HBTU/HOBt (i.e. 312 mg/136 mg/379.5 mg) and 12 equivalents of DIEA in NMP (i.e. 210 μl). After 50 minutes' reaction and washing of the support to eliminate the excess reagent, a Kaiser test is conducted to check for the absence of free —$NH_2$ functions.

Second coupling:
Fmoc-Lys-Boc-OH (4 equivalents, or 187.4 mg).
Number of equivalents HOBt/HBTU/DIEA:
4/4/12 (54.4 mg/151.4 mg/210 μl);
Reaction time: 50 minutes.
Third coupling:
Fmoc-Lys-Fmoc-OH (4 equivalents, or 236.3 mg).
Number of equivalents HOBt/HBTU/DIEA:
4/4/12 (54.4 mg/151.4 mg/210 μl);
Reaction time: 50 minutes.
Fourth coupling:
Fmoc-Lys-Fmoc-OH (4 equivalents, or 473 mg).
Number of equivalents HOBt/HBTU/DIEA:
4/4/12 (109 mg/303.6 mg/420 μl);
Reaction time: 50 minutes.
Fifth coupling:
Fmoc-Lys-Fmoc-OH (2.5 equivalents, or 590 mg).
Number of equivalents HOBt/HBTU/DIEA:
2.5/2.5/7.5 (136 mg/379.5 mg/579 μl);
Reaction time: 50 minutes.
Sixth coupling:
Fmoc-Lys-Fmoc-OH (2.5 equivalents, or 1.18 g).
Number of equivalents HOBt/HBTU/DIEA:
2.5/2.5/7.5 (272 mg/759 mg/1158 μl);
Reaction time: 50 minutes.
Coupling of the chloroacetic acid (8 equivalents per —$NH_2$ function) is carried out twice using diisoproplycarbodiimide as an activation agent.

Deprotection of the support and of the amino acids is carried out using 10 ml of TFA/$H_2O$/anisole (95/2.5/2.5 by volume) for 2 hours at room temperature. The support is then washed with dichloromethane and ether before being dried at reduced pressure.

Periodic oxidation is carried out after swelling of the support with 5 ml of water/acetic acid (2/1 by volume) for 15 minutes, using 128 mg of sodium periodate dissolved in 2 ml of water/acetic acid (5/1 by volume). After 2 minutes' reaction, the support is filtered and then washed with water (twice 6 ml). The filtrates are collected and 200 μl of ethylene glycol are added in order to stop the oxidation reaction.

The product is purified by HPLC on a C18 Hyperprep column (15×200 mm) using a linear gradient (0-50% of eluent B for 100 minutes), at the rate of 3 ml/min, with absorbance measurement being carried out at 215 nm.

Eluent A: water containing 0.05% by volume of TFA.
Eluent B: water/acetonitrile (1/4 by volume) containing 0.05% of TFA.

The pure fractions are collected and freeze dried. 71 mg of purified peptide 20 are obtained, i.e. a yield of 20%.

EXAMPLE 9

Chemical Ligations Implementing the Peptides According to the Invention, Functionalised in C-terminal Position with an α-oxoaldehyde 1) Synthesis of Peptides 10, 12 and 14
These peptides are shown in FIG. 3.
Synthesis of Peptides 10 and 14
Peptides 10 and 14 were prepared on a 4-methyl-benzhydrylamine polystyrene resin (0.57 mmol of reactive amine functions per gram of resin; Applied Biosystem, Foster City, USA) according to the protocol described by R. B. Merrifield in J. Am. Chem. Soc., 1963, 85, 2149 and in Science, 1986, 232, 341 (Boc/benzyl strategy). The automatic peptidic synthesiser is an 431A Applied Biosystem (Foster City, USA) apparatus implementing the protocol described in Int. J. Pept. Protein Res., 1992, 40, 180.

The amino acids protected by a Boc functional group were supplied by Propeptide (Vert-Le-Petit, France). The protective functional groups of the side chains are as follows: Arg (tosyl), Asp (O-cyclohexyl), Asn (trityl), Lys (2-chlorobenzylo-xycarbonyl), Gln (trityl), Tyr (2-bromobenzyloxy-carbonyl), Glu (O-cyclohexyl), Asn (trityl), His (dinitrophenyl), Ser (O-benzyl), Cys (para-methylbenzyl), Trp (formyl).

In the case of peptide 10, the lysine to be modified with the N-amination reagent N-Boc-3-(4-cyanophenyl) oxaziridine (BCPO), was introduced in the form Boc-L-Lys (Fmoc)-OH, supplied by France Biochem (Meudon, France). The Fmoc group is eliminated with a mixture of 20% piperidine in DMF after the assembly of the amino acids. The N-amination protocol is the one described in connection with Applied Biosystem 431A automatic synthesiser (Tetrahedron Letters, 1996, 37, 7259-7262 and J. Peptide Res., 1998, 52, 180-184).

Peptide 10 was de-protected and separated from the support using liquid hydrogen fluoruide (HF), in the following proportions: dry support/HF/paracresol/parathiocresol, 1 g/10 ml/0.75 g/0.25 g, for 1 h 30 and at 0° C. The hydrofluoric acid is then eliminated at reduced pressure at 0° C., and then the crude peptide is precipitated in 200 ml of cold ether. The precipitate is centrifuged, dissolved in a water/acetic acid mixture and then freeze dried.

The crude peptide is purified by RP-HPLC on a Hyperprep column, with the help of a linear gradient of a water/acetonitrile eluent containing 0.05% of trifluoroacetic acid. The peptide 10 yield is 16%. Its mass, obtained using electrospray mass spectrometry, is 2330.6.

As to peptide 14, the formyl groups located on the tryptophanes were removed, in solid phase, by washing the support with a piperidine/DMF mixture (1/10 by volume) for 3 h. The support, on which peptide 14 is grafted, is then washed with DMF, and then ether, and vacuum dried.

Final deprotection and the cleavage of the peptide from the support are effected using a dry support/HF/para-cresol/parathiocresol mixture (1.5 g/10 ml/0.75 g/0.25 g) for 1 h 30 and at 0° C. The crude peptide is precipitated in ether, centrifuged and then dissolved in a water/acetic acid mixture (3/1 by volume), and finally freeze dried. Purification by RP-HPLC is carried out using a 15×300 mm nucleosil C18 column, supplied by Macherey Nagel (Paris, France), in the same way as for peptide 10. The peptide 14 yield is 44.6%. Its mass, obtained using plasma desorption mass spectrometry, is 1823.3.

Synthesis of the $BocNHNHCH_2COOH$ Functional Group 31.36 g (0.144 mmol) of $Boc_2O$ are added to 15.80 ml (0.131 mmol) of N-methylmorpholine and 20 g (0.131 mmol) of ethylhydrazinoacetate hydrochloride dissolved in 130 ml of a water/ethanol mixture (1/1 by volume). The reaction mixture is stirred for 24 h at room temperature, and then 11.5 g (0.288 mmol) of sodium hydroxide are added for 15 minutes. After stirring for 3 h 45, the mixture is diluted in 100 ml of water and saturated with sodium chloride. The pH is adjusted to 3.0 using solid citric acid.

The resulting aqueous solution is extracted with ether (8 times 50 ml). The successive extracts are collected, washed with water (twice 50 ml), dried with sodium sulphate and concentrated at reduced pressure.

The crude product obtained is re-crystallised in a tert-butylmethyl-ether/methanol mixture (10/1 by volume) to give 12.2 g of a white solid (yield: 43%), the elemental analysis obtained for which is C: 44.52%, H: 7.69%, N: 15.02% and O: 33.57%. The RMN $^1H$ analysis of this product is as follows: (300 MHz, MeOH-$d_4$): 1.44 (tert-butyl), 4.06 (C$H_2$CO).

Synthesis of Peptide 12

The peptide 12 was prepared using 0.25 mmol of a Rink Amide resin (0.47 mmol/g, France Biochem, Meudon, France), that is to say a 4-(2',4'-dimethoxyphenyl-Fmoc-aminomethyl)-phenoxy resin, in the same way as for peptides 3-5 and 9 (example 4).

4 pre-synthesised equivalents of $BocNHNHCH_2COOH$ were grafted onto the N-terminal end of the peptide using a BOP/DIEA mixture (4 eq./12 eq.) in DMF.

Peptide 12 is separated from the support and de-protected using 10 ml of a trifluoroacetic acid/thioanisole/water mixture (90/5/5 by volume) for 2 h 30. The mixture containing the de-protected peptide is added drop by drop to 200 ml of cold ether. The precipitate is centrifuged, resuspended in a water/acetic acid mixture (9/1 by volume) and then freeze dried.

The crude peptide is purified by RP-HPLC using a 15×300 mm C18 Hyperprep column. Use is made of a linear gradient of 10 to 40% of eluent B for 100 minutes (eluent B: water/$CH_3CN$ (1/4 by volume), containing 0.05% of TFA; eluent A: water containing 0.05% of TFA by volume), at the rate of 3 ml/min, absorbance being measured at 215 nm.

The pH of the fractions containing the peptide 12 is adjusted to 6.8 with the 0.1 M Tris buffer, prior to freeze drying.

The solid obtained (537.9 mg) contains 20.9% of peptide 12, determined as for peptide 5. Whence a yield of 28.5% in terms of peptide 12.

Figure 7:
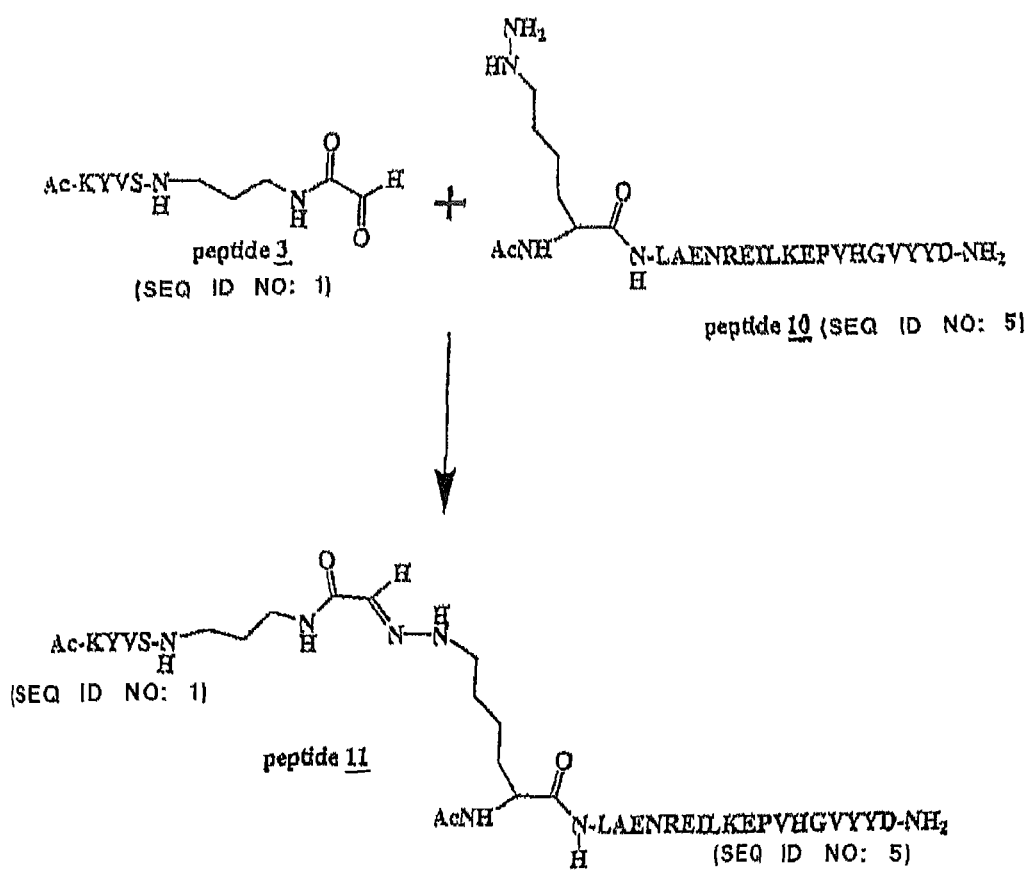
FIGS. 7 and 8 represent chemical ligation reactions of the hydrazone type using peptides according to the invention.

2) Ligation of the Hydrazone Type Between Peptide 10 and Peptide 3 (FIG. 7)

11.2 mg (3.7 μmol) of peptide 10 and 3.2 mg (4.2 μmol) of peptide 3, obtained according to Example 4, are dissolved in 2.25 ml of citrate/phosphate buffer (pH 6.0) and in 560 μl of dimethylsulfoxide, at room temperature. After 48 h, the mixture is purified by RP-HPLC on a 15×300 mm C18 Hyperprep column. After freeze drying, 6.6 mg of peptide 11 are obtained, i.e. a yield of 48.8%.

Figure 8:
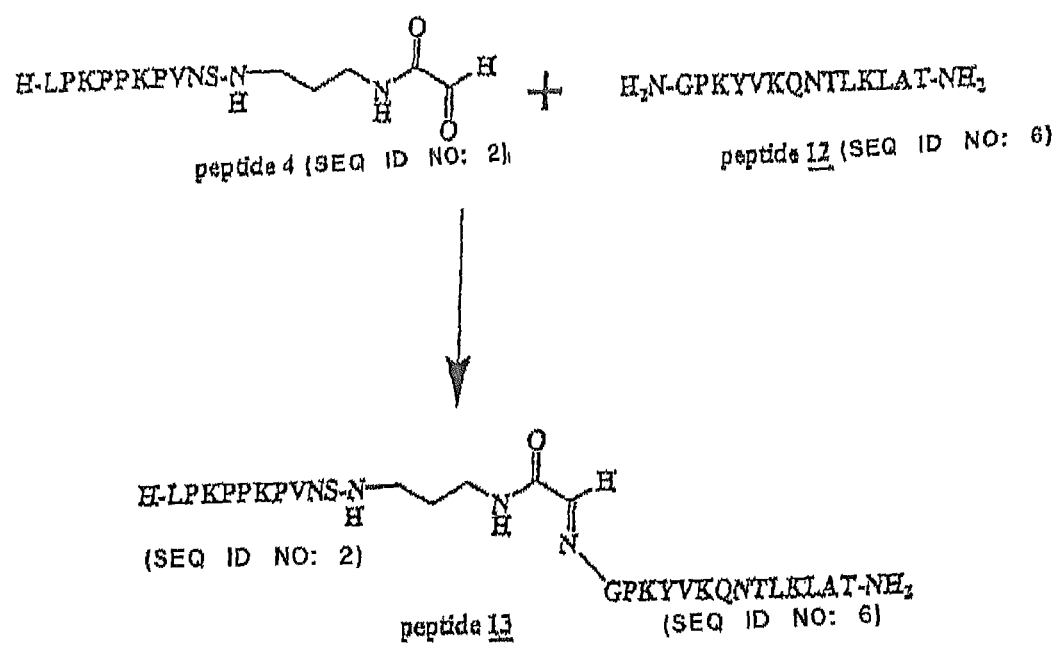

3) Ligation of the Hydrazone Type Between Peptide 12 and Peptide 4 (FIG. 8)

15.65 mg (2.08 μmol) of peptide 12 and 5.87 mg (4.15 μmol) of peptide 4, obtained according to example 4, are dissolved in 1.5 ml of citrate phosphate buffer (pH 6.0), at room temperature. After 48 h, the mixture is purified by RP-HPLC, as described in 2). After freeze drying, 6.2 mg of peptide 13, i.e. a yield of 47.0%, are obtained.

FIGS. 7 and 8 show that chemical ligation of the hydrazone type between two peptidic fragments can be achieved with good yields, with one of the fragments (peptide 10 in FIG. 7 and peptide 12 in FIG. 8) bearing, at its N-terminal end, a hydrazine function, whereas the other peptidic fragment (peptide 3 in FIG. 7 and peptide 4 in FIG. 8) bears, at its C-terminal end, an α-oxoaldehyde function, this function having been introduced by means of peptidic synthesis on a support according to the invention.

Figure 9:
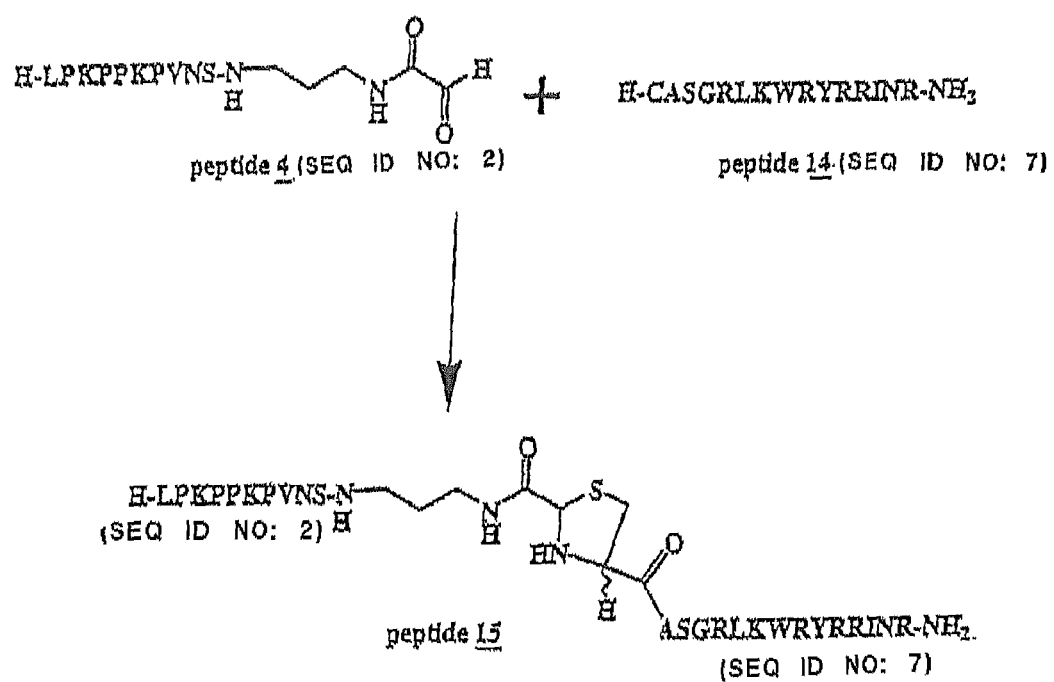
FIG. 9 represents a chemical ligation reaction of the thiazolidine type using a peptide according to the invention.

4) Ligation of the Thiazolidine Type Between Peptide 14 and Peptide 4 (FIG. 9)

The reaction was carried out under nitrogen atmosphere. 6 mg (2.29 μmol) of peptide 14 are dissolved in 680 μl of a 1/1 mixture (by volume) of NMP and citrate/phosphate buffer (pH 5.1). There are then added 328 μg (1.15 μmol) of tris (2-carboxyethyl)-phosphine hydrochloride dissolved in 48.3 μl of the aforementioned buffer, followed by 6.49 mg (5.58 μmol) of peptide 4 dissolved in 680 μl of buffer/NMP (1/1 by volume). The mixture is stirred for 1 h at room temperature, and then left at 37° C. for 20 h.

The mixture is then purified by RP-HPLC, as described in 2). After freeze drying, 4.8 mg of peptide 15, i.e. a yield of 53.7%, are obtained.

FIG. 9 thus shows that a peptide bearing an α-oxoaldehyde function at its C-terminal end, obtained by means of peptidic synthesis carried out on a support according to the invention, can be chemically bonded, with a good yield, to a peptide bearing a cysteine residue (β-amino-thiol function) in N-terminal position, giving rise to the formation of a thiazolidine bond between the two peptidic fragments.

Figure 10:
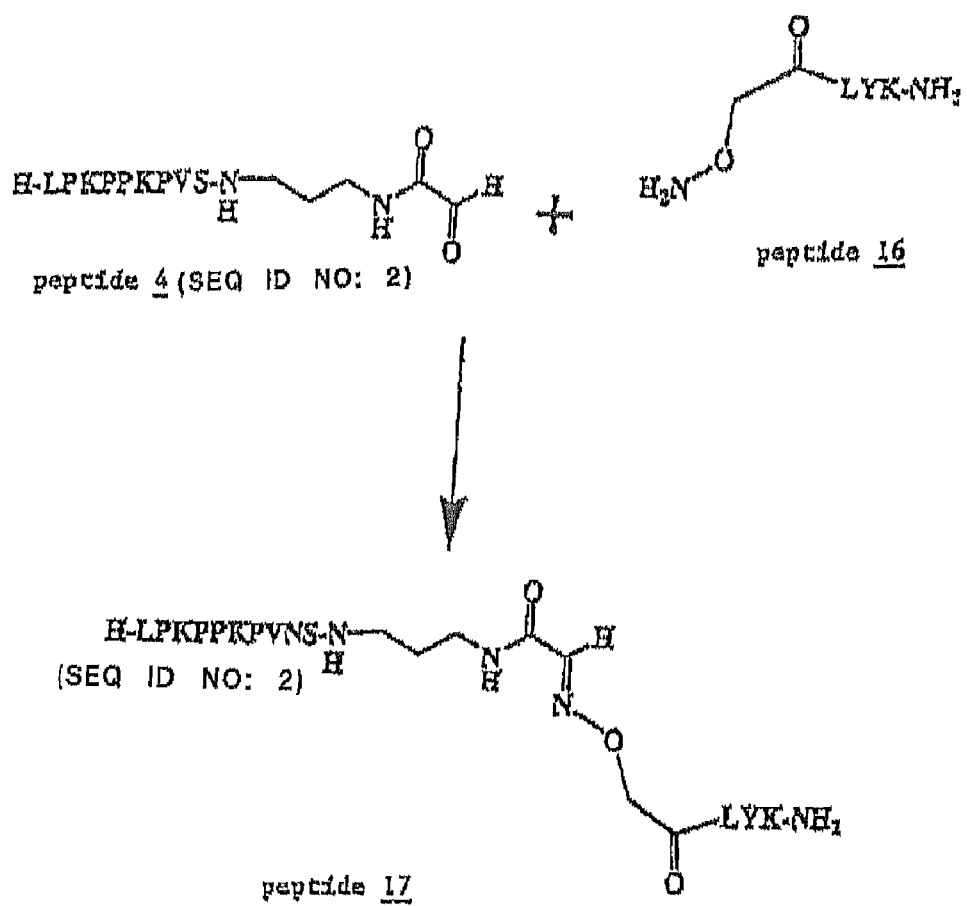
FIG. 10 represents a chemical ligation reaction of the oxime type using a peptide according to the invention.

5) Ligation of the Oxime Type Between Peptide 16 and Peptide 4 (FIG. 10)

Synthesis of Peptide 16

This tripeptide was synthesised using the Boc/benzyl strategy from 0.5 mmol of tBoc-Leu-OCH$_2$-PAM resin (667 mg, charge: 0.75 mmol/g). After deprotection of the leucine with a TFA/CH$_2$Cl$_2$ mixture (1/1 by volume, for 30 minutes), the amino acids, Boc-L-Tyr (2-bromobenzyloxy-carbonyl)-OH (988.4 mg, 4 equivalents, single coupling) and Boc-Lys (2-chlorobenzyloxycarbonyl)-OH (428.3 mg, 4 equivalents, double coupling) were activated for 1 minute with HBTU/DIEA (756 mg, or 4 equivalents/1044 μL, or 12 equivalents) before being added to the resin solvated by a minimum volume of NMP. Boc-HN—O—CH$_2$—CO$_2$H (191.2 mg, or 2 equivalents) and BOP (440 mg, or 2 equivalents) were then added to the resin solvated by a minimum volume of NMP. The DIEA (500 μl, or 6 equivalents) is added in a single step and the suspension is stirred for 45 minutes at room temperature.

Deprotection and cleavage of the peptide from the support (on 0.8 g) were carried out with HF/paracresol/parathiocresol (10 ml/0.2 g/0.2 g) for 1 h 30 at 0° C. After evaporation of the hydrofluoric acid, the residue is suspended in TFA, filtered, and the filtrate is added drop by drop to cold ether. The precipitate is centrifuged, and purified by RP-HPLC on a Hyperprep C18 column (20×300 mm). Eluent A: TFA, 0.05% in $H_2O$ and eluent B: TFA, 0.05% in isopropanol/$H_2O$: 3/2. Gradient 0-10% of eluent B in 150 minutes, rate: 1 ml/min, detection at 215 nm.

Chemical Ligation 3.53 mg of peptide 4, obtained according to Example 4, are dissolved in 200 µl of water. Thereto are added 3.25 mg of peptide 16 dissolved in 1.2 ml of sodium acetate/acetic acid buffer, pH 4.6, prepared by mixing 510 µl of 0.2 M acetic acid, with 492 µl of 0.2 M sodium acetate, and by topping up to 2 ml with water.

After 42 hours' reaction, the peptide 17 is purified by RP-HPLC as described in 2). After freeze drying, 4.0 mg of peptide 17, i.e. a yield of 78.13%, are obtained.

FIG. 10 shows that a peptide bearing an α-oxoaldehyde function at its C-terminal end, obtained by means of peptidic synthesis carried out on a support according to the invention, can be chemically bonded, with a very good yield, to a peptide bearing a hydroxylamine function in N-terminal position, giving rise to the formation of an oxime bond between the two peptidic fragments.

EXAMPLE 10

Recycling a Support According to the Invention After its use in a Process for the Synthesis of Organic Compounds Comprising at Least One α-oxoaldehyde Function Periodic oxidation carried out in the course of the process according to the invention, for the synthesis of organic compounds comprising at least an α-oxoaldehyde function, also generates an aldehyde function on the solid support, that is to say the formula V product:

$$OHC-(A)_n-Z-(B)_m-S \quad (V)$$

In this example, the regeneration of a support bearing an amine function at its end is described, in the case of the group $-(A)_n-Z-(B)_m-$ is an amide group ($-CO-NH-$), that is to say if the solid support, after the periodic oxidation step, corresponds to the formula VI:

$$OHC-CO-NH-S \quad (VI)$$

One or more amine functions can be generated from the α-oxoaldehyde by reductive amination.

For example, the formula VI product can be reacted with $NH_4Br/NaCNBH_3$ in methanol, which will give the following formula VII product:

$$H_2N-CH_2-CO-NH-S \quad (VII)$$

It is also possible to react the formula V product with an $NaCNBH_3$/1,3-diaminopropane mixture (or another diamine having the formula $H_2N-(CH_2)_a-NH_2$) in methanol, which will give the following formula VIII product:

$$H_2N-(CH_2)_a-NH-CH_2-CO-NH-S \quad (VIII)$$

In this latter case, the use of a primary diamine makes it possible to create, on the regenerated support, a primary amine function and a secondary amine function, which multiplies the charge of the support by two. The use of a secondary diamine would have made it possible to create on the support a tertiary amine and a secondary amine, the initial charge of the support thus being preserved.

The reducing amination reactions described above are perfectly familiar to a person skilled in the art, as evidenced by the work entitled "*Reduction by the alumino- and borohydrides in organic synthesis*", J. Seyden-Penne, 1991, VCH Publishers Inc./Lavoisier, N.Y.

Once the reducing amination has been completed, it is then possible to regenerate a formula I support according to the invention, by reacting the product obtained (product VII or product VIII) with a formula II compound as previously described.

For example, if the reductive amination is carried out with $NH_4Br/NaCNBH_3$, or with a secondary diamine, the reaction of the reduction product, for example the formula VII compound, with the formula II compound gives the following support:

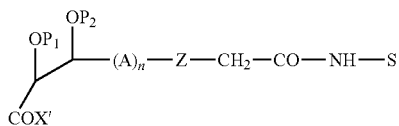

If the reductive amination is carried out with a primary diamine, for example with a diamine having the formula $H_2N-(CH_2)_3-NH_2$, the reaction of the reduction product, for example the formula VIII compound, in which a=3, with the formula II compound gives the following support:

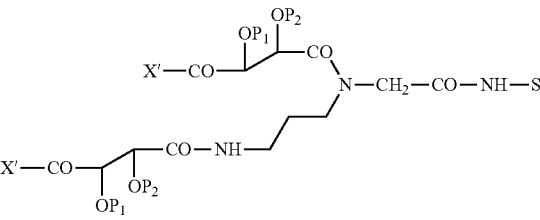

These examples thus demonstrate the usefulness of the peptides according to the invention, which bear an α-oxoaldehyde function at their C-terminal end and which are obtained using a support according to the present invention, in the context of chemical ligation.

EXAMPLE 11

Synthesis of an Oligonucleotide Functionalised by an α-oxoaldehyde Using a Support According to the Invention The support used corresponds to the general formula I described above, wherein n=m=0, P1 and P2 represent the $CH_3CO-$ acetyl groups, X' represents a $-OH$ group, Z represents an amide bond and S is a borosilicate glass. Such a support is obtained by reacting a derivative of tartaric acid, the hydroxyl functions of which in positions 1, 2 are protected by acetyl groups, with a borosilicate glass functionalised by an amine function, functionalisation of this glass being accomplished using techniques well known to persons skilled in the art, and described, for example, in "*Oligonucleotides synthesis: a practical approach*", 1984, M. J. GAIT Ed., IRL Press, Washington D.C. The derivative of the tartaric acid used is, for example, diacetyl-tartaric anhydride (cyclic anhydride), or tartaric acid, the hydroxyl functions of which in positions 1, 2 are protected by acetyl groups and which is activated by BOP.

The support obtained is functionalised with 1,3-diaminopropane, again using BOP as an activation reagent. The oligonucleotides are bound to the resulting support in accordance with the following references: "*Oligonucleotides synthesis: a practical approach*", 1984, M. J. GAIT Ed., IRL Press, Washington, D.C., "*Current protocols in molecular biology*", 1994, John Wiley & Sons Ed., sections 2.11.1-2.11.25.

A first deoxynucleotidic base is bound, for example, via a carbamate bond: reaction of the support obtained above with phosgene (creation of an isocyanate function on the support), followed by reaction of the deoxynucleotide, the hydroxyl function of which in position 5' of the sugar is protected by a dimethoxytrityl group, the deoxynucleotide being bound on the support by its hydroxyl function in position 3'. The base of the deoxynucleotide is protected by acyl functional groups, for example a benzoyl or a methyl-2-propanoyl.

Step by step, the successive binding of several deoxynucleotidic bases permits the solid phase synthesis of DNA. Similarly, an RNA synthesis according to this same protocol could be effected, the hydroxyl in position 2' of the sugar then being suitably protected, for example by a tert-butyldimethylsilyl group.

When the synthesis is completed, the P1 and P2 groups of the support according to the invention are eliminated by a treatment in basic medium, for example ammonium hydroxide. This treatment at the same time permits deprotection of the oligonucleotide bases. A solid phase periodic oxidation step, such as the one described in Example 4, then enables the oligonucleotide (DNA or RNA) functionalised by an α-oxoaldehyde to be obtained. In the case of RNA synthesis, the aforementioned treatment in a basic medium is preceded by a step of deprotection of the hydroxyl group in position 2' of the sugar, for example with $Bu_4N^+$, $F^-$.

EXAMPLE 12

Synthesis of a Peptide Functionalised with an α-oxoaldehyde Using a Support According to the Invention and Use of this Peptide as a Diagnostic Reagent 1) Preparation of a Support According to the Invention Use is made of a PEGA® amino resin with a dry charge equal to 0.3 mmol/g and a wet charge (in methanol) of 0.06 mmol/g. The amount of resin used is 25.1 g, or 1.5 mmol. The resin is washed three times with dichloromethane, three times with 5% DIEA in dichloromethane, and then three times with DMF. The resin is then soaked with a minimum volume of DMF.

To 108 µl of water (6 mmol) are added 13.11 ml (69.45 µmol) of (+)-dimethyl-2,3-O-isopropylidene-D-tartrate, followed by 897 µl of DBU. The mixture is stirred for 1 hour at room temperature, and than added to the resin prepared above. After stirring for 30 seconds, 3122 mg (6 mmol) of PyBOP (benzotriazol-1-yl-oxy-tris-pyrrolidino-phosphonium hexa-fluorophosphate). The reaction medium is left for 40 minutes at room temperature, while being stirred. The resin is then washed 4 times using DMF, and then 4 times with dichloromethane. A formula I support according to the invention is obtained that is identical with support 6 prepared according to Example 2.

4,7,10-trioxa-1,13-tridecanediamine (TTD) is grafted onto the end of the support in order to introduce a free amine function on the surface of the latter, permitting subsequent synthesis of peptides. For this purpose, the support is soaked with a minimum volume of DMF, and then 6.61 ml of TTD are added (30 mmol, or 20 times more than the initial quantity of PEGA® amino resin). After stirring for 1 hour, the support is washed 5 times with DMF, twice with dichloromethane and twice with ether, and then vacuum dried. The support obtained has a charge of 0.18 mmol/g, determined after coupling the Fmoc-Gly-OH with a known quantity of support and analyse of the piperidine/dibenzofulvene adduct by UV spectrometry.

2) Synthesis of a Peptide Functionalised by an αa-oxoaldehyde

The peptide having the following sequence:
AVDTGSGGGGQPHDTAPRGARKKQ (SEQ ID NO: 9)
is synthesised on the solid support prepared above using the Fmoc/tert-butyl strategy in a peptide synthesiser of the Pioneer trade-mark (Perceptive Biosystems). The groups protecting the side chains are as follows: ($^t$Bu: tert-butyl; Trt; trityl; Boc: tert-butyloxycarbonyl; Pbf: 2,2,4,6,7-pentamethyldihydrobenzofuran-5-sulfonyl): Arg(Pbf), Asn (Trt), Asp (O$^t$Bu), Cys (Trt), Gln (Trt), Glu (O$^t$Bu), His (Trt), Ser ($^t$Bu), Thr ($^t$Bu), Trp (Boc), Lys (Boc), Tyr ($^t$Bu).

Peptidic synthesis is carried out with 0.555 g of support. The amino acids are used in excess quantity of 10 and activated by HOBt/HBTU (0.5 M) in DMF. For each amino acid, double coupling is carried out, followed by a capping.

Once the peptidic synthesis is completed, the peptide, bearing a terminal primary amine function, is de-protected on the support with a TFA/water/anisole mixture (95/2.5/2.5). The support is washed with dichloromethane (3×2 minutes) and ethyl ether (2×2 minutes), and then vacuum dried.

The periodic cleavage generating the terminal α-oxoaldehyde function is carried out in the following steps; suspension of the support in 5 ml of acetic acid, addition of 6 equivalents of $NaIO_4$, stirring for 5 minutes, addition of 100 µl of ethanolamine and stirring for 1 minute.

Figure 11:
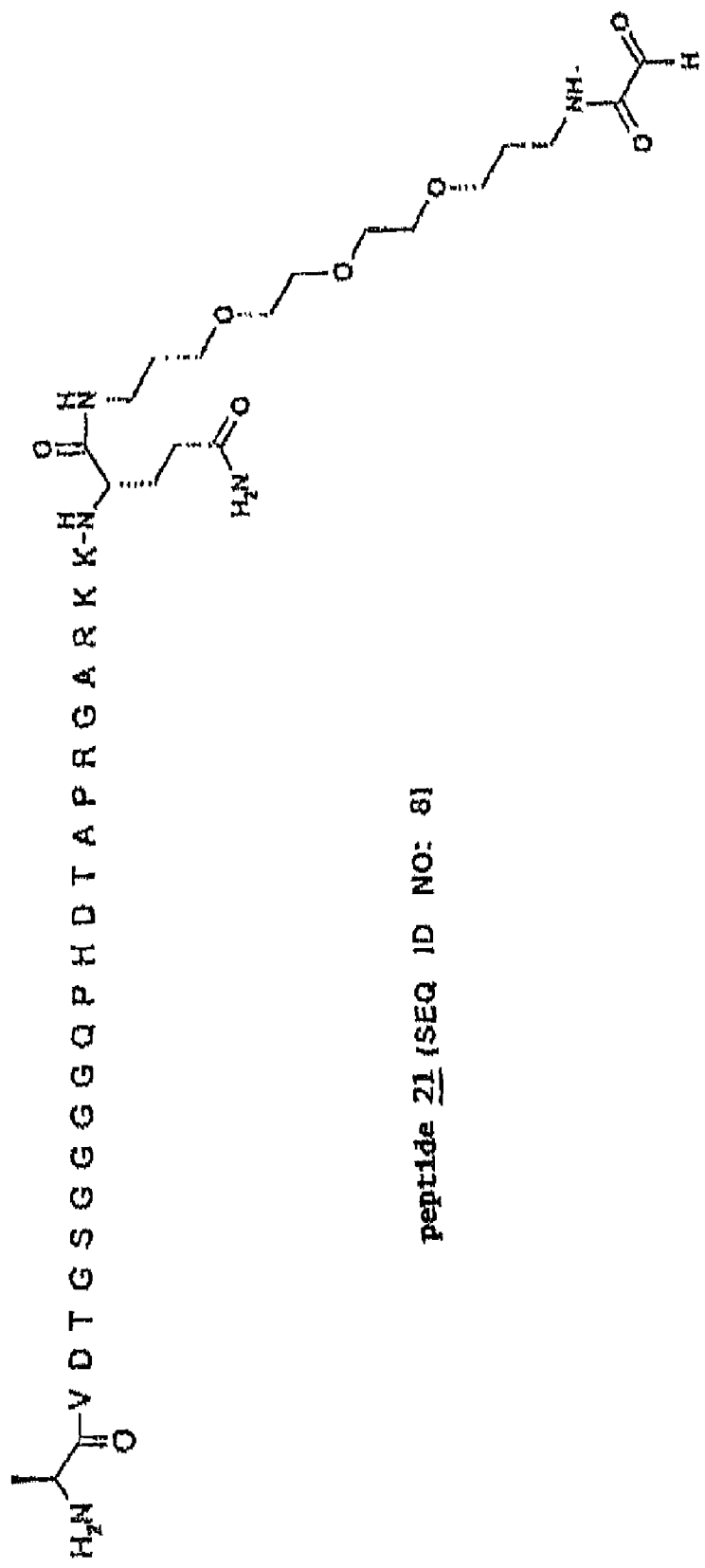
FIG. 11 represents the peptide 21 (SEQ ID NO: 8), bearing a terminal α-oxoaldehyde function and synthesised using a support according to the invention.

The solution recovered, which contains peptide 21 (FIG. 11) bearing a terminal α-oxoaldehyde function, is purified by desalting on a G10 Sephadex® column (60 cm×2.5 cm). Chromatography conditions are as follows:
  solvent: 5% acetic acid,
  solvent flow rate: 0.7 ml/minute,
  pump speed: 30 rpm,
  wavelength for detection of the peptide: 240 nm.

The chromatographic fraction corresponding to the peptide is freeze dried, and then the peptide is purified by preparative RP-HPLC on a C18 column. Chromatography conditions are as follows:
  stationary phase: C18 NUCLEOSIL®,
  mobile phase: water containing 0.05% of TFA, with a linear gradient of 0 to 80% of acetonitrile,
  temperature: 60° C.,
  flow rate of mobile phase: 3 ml/minute,
  wavelength for detection of the peptide: 215 nm.

The chromatographic fraction corresponding to the peptide is freeze dried, and then characterised. The homogeneity of the peptide is confirmed by analytical HPLC on a C18-VYDAC® column eluted with the same solvent as above. The identity of the peptide is confirmed by determining the amino acid composition, by total acid hydrolysis for 24 hours with an HCl 6N/phenol (10/1) mixture and by mass spectrometry recorded on a Bio Ion 20 plasma spectrometer supplied by the company Bio Ion AB, Upsala, Sweden (mass calculated: 2605 g/mol; found: 2605 g/mol).

3) Diagnostic Reagent of the ELISA Type Prepared Using this Peptide

Microtitration plate wells (Carbo-bind, New York, USA) are covered with the above synthesised peptide (0.1 ml of peptide with a concentration of 0.5 µg/ml in a sodium acetate buffer, 0.1 M, pH 5.5) for 1 hour and in a humidified atmosphere.

Each well then undergoes 3 washing operations in an automatic washer with a 0.01 M phosphate buffer including 1.8% of NaCl, pH 7.4 (PBS) and the excess bonding sites are blocked by whole milk powder (addition of 0.2 ml of milk powder at 2.5% in PBS), incubation being carried out at 37° C. for 60 minutes.

After 3 washing operations carried out using PBS including 0.05% of Tween 20 (PBS-T buffer, marketed by Sigma), the human serums for testing are diluted to 1/50th in PBS including 2.5% of whole milk and 0.5% of Tween 20. 0.1 ml of these diluted serums are incubated in wells containing the peptide 21 synthesised above, for 120 minutes at 37° C.

After 4 washing operations using PBS-T, 0.1 ml of peroxydase-goat-antibody-anti-human IgG-A-M conjugates (Pasteur Diagnosis), diluted to 1/10000th in PBS buffer including 0.5% of Tween 20 and 2.5% of whole milk, are incubated for 60 minutes at 37° C.

After 4 washing operations using PBS-T, the peroxidase activity of the conjugated antibody, which bonds to the Ig fixed onto the support, is measured using as a substrate 0.1 ml of o-phenylenediamine dihydrochloride and $H_2O_2$, in a citrate buffer, 0.05 M, pH 5.5, for 30 minutes in the dark and at room temperature.

The reaction is capped by the addition of $H_2SO_4$ 2N (25 µl). Absorbance is recorded with reference to a blank at 492 nm with a multi-channel automatic reader (Mr 5000, Dynatech).

The mean value $A_{492}$+3 standard deviations of the negative EBV (Epstein-Barr Virus) samples is used as a threshold value in the ELISA tests. A second way of expressing the results is to calculate the ratio R: [$A_{492}$ positive serum]/[mean value $A_{492}$+3 standard deviations) negative serums], with the serums considered positive having to have a ratio R greater than 1.

The results obtained for the ELISA tests carried out on the Carbo-Bind microtitration plates are set out in Table I. These same tests were carried out using a non-covalent conventional microtitration plate (Nunc, Maxisorp, Rocksilde, Denmark). Comparison of the R ratios for the two tests shows that the Carbo-Bind microtitration plates, on which the peptides are covalently bound, make it possible to orientate the peptide, to improve the signal of the positive serums and to reduce the signal and the dispersal of the negative serums, as well as to reduce background noise.

TABLE I

| Positive serums | Carbo-Bind microtitration plate | | Conventional microtitration plate | |
|---|---|---|---|---|
| | Absorbance | Ratio R | Absorbance | Ratio R |
| 1 | 0.58 | 4.14 | 1.56 | 1.71 |
| 2 | 0.27 | 1.93 | 0.61 | 0.67 |
| 3 | 0.33 | 2.36 | 1.62 | 1.78 |
| 4 | 0.17 | 1.21 | 1.04 | 1.14 |
| 5 | 0.57 | 4.07 | 1.40 | 1.54 |
| 6 | 1.40 | 10.00 | 1.52 | 1.67 |
| 7 | 0.04 | 0.29 | 0.85 | 0.93 |
| 8 | 0.14 | 1.00 | 0.41 | 0.45 |
| 9 | 0.05 | 0.36 | 0.80 | 0.88 |
| 10 | 0.43 | 3.07 | 1.00 | 1.10 |
| 11 | 0.55 | 3.93 | 1.55 | 1.70 |
| 12 | 0.08 | 0.57 | 0.64 | 0.70 |
| 13 | 1.62 | 11.57 | 0.93 | 1.02 |
| 14 | 1.05 | 7.50 | 1.80 | 1.98 |
| 15 | 0.07 | 0.50 | 0.52 | 0.57 |
| 16 | 0.73 | 5.21 | 0.75 | 0.82 |
| 17 | 1.56 | 11.14 | 1.83 | 2.01 |
| 18 | 1.72 | 12.29 | 1.50 | 1.65 |
| 19 | 1.33 | 9.50 | 1.56 | 1.71 |
| 20 | 1.61 | 11.50 | 2.03 | 2.23 |
| 21 | 0.23 | 1.64 | 0.42 | 0.46 |
| 22 | 0.36 | 2.57 | 0.87 | 0.96 |
| 23 | 1.67 | 11.93 | 1.48 | 1.63 |

| Negative serums | Absorbance | Absorbance |
|---|---|---|
| 1 | 0.05 | 0.26 |
| 2 | 0.03 | 0.22 |
| 3 | 0.03 | 0.21 |
| 4 | 0.02 | 0.05 |
| 5 | 0.07 | 0.25 |
| 6 | 0.02 | 0.17 |
| 7 | 0.03 | 0.11 |
| 8 | 0.07 | 0.34 |
| 9 | 0.09 | 0.47 |
| 10 | 0.04 | 0.14 |
| 11 | 0.03 | 0.10 |
| 12 | 0.09 | 0.97 |
| 13 | 0.06 | 0.21 |
| 14 | 0.04 | 0.17 |
| 15 | 0.06 | 0.38 |
| 16 | 0.04 | 0.09 |
| 17 | 0.03 | 0.23 |
| 18 | 0.03 | 0.09 |
| 19 | 0.07 | 0.14 |
| 20 | 0.17 | 0.74 |
| 21 | 0.04 | 0.11 |
| 22 | 0.04 | 0.13 |
| 23 | 0.07 | 0.20 |
| Mean value | 0.05 | 0.25 |
| Standard deviation | 0.03 | 0.22 |
| Positivity threshold | 0.14 | 0.91 |

The invention claimed is:

1. A functionalized solid support according to formula I for the synthesis of compounds comprising at least one α-oxoaldehyde:

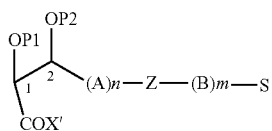

Formula (I)

wherein:
S is a solid support having a surface that is well solvated in an aqueous or partially aqueous medium, wherein S is a polyacrylamide-polyethyleneglycol resin,
m and n represent 1,
B is a —(CH$_2$)$_2$—CO—NH— chain,
Z is an amide group,
A is a —CO—NH—(CH$_2$)$_3$— chain,
P1 and P2 form together an isopropylidene protective group, protecting the hydroxyl functions in positions 1, 2; and;
X' is a —NH—(CH$_2$)$_3$—NH$_2$ chain.

2. A process for preparing the formula I support according to claim 1, comprising reacting:
a functionalised solid support having the formula S—(B)$_m$—Y, wherein B, S and m are as described in claim 1 and Y represents an amine,
with a compound selected from the group constituted by the cyclic anhydrides of tartaric acid and the compounds of formula II:

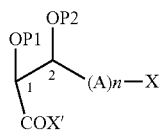

(II)

wherein n, A, P1, P2 and X' are as defined in claim 1 and X represents a carboxy group.

3. A process for preparing the formula I support according to claim 1, comprising reacting:
   a functionalised solid support having the formula S—(B)$_m$—Y, wherein B, S and m are as described in claim 1 and Y represents a carboxy group,
   with a compound selected from the group constituted by the cyclic anhydrides of tartaric acid and the compounds of formula II:

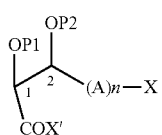
(II)

wherein n=1 and A, P1, P2 and X' are as defined in claim 1 and X represents an amine.

4. The process according to claim 2 or claim 3, wherein the carboxy group is transformed to a functional group selected from a group consisting of the following functional groups:
   —COOR$_2$, —COO$^-$ transformed by an electrophilic activating agent, and —N=C=O (isocyanate), where R$_2$ represents a hydrogen atom or an aryl or a heteroaryl group, said aryl group and heteroaryl group optionally being partially or completely substituted by one or more halogen atoms, one or more amino, hydroxy, alcoxy, aryloxy, alkylthio or arylthio groups.

5. The process according to claim 2 or claim 3, wherein the amine group is selected from the family consisting of the following functional groups:
   —NHR$_5$, —CONR$_5$NH$_2$, —N[R$_5$(CO)]NH$_2$, N[R$_5$O(CO)]NH$_2$, —N[R$_5$NH(CO)]NH$_2$, and (CO)ONH$_2$, where R$_5$ represents a hydrogen atom or an aryl or a heteroaryl group, said aryl group and heteroaryl group optionally being partially or completely substituted by one or more halogen atoms, one or more amino, hydroxy, alcoxy, aryloxy, alkylthio or arylthio groups.

6. The process according to claim 2, wherein P1 and P2, groups protecting hydroxyl functions in positions 1,2, are introduced after the reaction of the solid support having the formula S—(B)$_m$—Y with the formula II compound, and before the formula I support according to claim 1 is used for the synthesis of compounds comprising at least one α-oxoaldehyde function.

7. The support according to claim 1, wherein one or more of the carbon atoms of A and/or B are substituted by a group according to formula II:

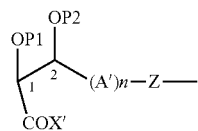
Formula II wherein A' is comprised of a chain of 1 to 18 carbon atoms, and wherein said carbon atom chain is linear, branched, cyclic, saturated or unsaturated, and wherein A' and A are the same or different and wherein P1 and P2 are defined as in claim 1.

8. The support according to claim 1, wherein said resin is the polyacrylamide resin sold under the trademark Spar®.

9. The support according to claim 1, wherein said resin is the polyacrylamide-polyethylene glycol resin sold under the trademark PEGA®.

10. The process according to claim 4, wherein the carboxyl group is transformed to: —COF, —COCl, —COBr, succinimidyl ester, or sulphosuccinimidylic ester.

* * * * *

SEQUENCE LISTING

<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: Peptide 3 sequence as described in Figure 3

<400> SEQUENCE: 1

Lys Tyr Val Ser
1

```
<210> SEQ ID NO 2
<211> LENGTH: 9
<212> TYPE: PRT
<213> ORGANISM: Artificial Sequence
<220> FEATURE:
<223> OTHER INFORMATION: Peptide 4 sequence as described in Figure 3

<400> SEQUENCE: 2

Leu Pro Lys Pro Pro Lys Pro Val Ser
1               5

<210> SEQ ID NO 3
<211> LENGTH: 17
<212> TYPE: PRT
<213> ORGANISM: Artificial Sequence
<220> FEATURE:
<223> OTHER INFORMATION: Peptide 5 sequence as described in Figure 3

<400> SEQUENCE: 3

Gln Tyr Ile Lys Ala Asn Ser Lys Phe Ile Gly Ile Thr Glu Leu Lys
1               5                   10                  15

Lys

<210> SEQ ID NO 4
<211> LENGTH: 4
<212> TYPE: PRT
<213> ORGANISM: Artificial Sequence
<220> FEATURE:
<223> OTHER INFORMATION: Peptide 9 sequence as described in Figure 3

<400> SEQUENCE: 4

Lys Tyr Val Ser
1

<210> SEQ ID NO 5
<211> LENGTH: 18
<212> TYPE: PRT
<213> ORGANISM: Artificial Sequence
<220> FEATURE:
<223> OTHER INFORMATION: Peptide 10 sequence as described in Figure 3

<400> SEQUENCE: 5

Leu Ala Glu Asn Arg Glu Ile Leu Lys Glu Pro Val His Gly Val Tyr
1               5                   10                  15

Tyr Asp

<210> SEQ ID NO 6
<211> LENGTH: 15
<212> TYPE: PRT
<213> ORGANISM: Artificial Sequence
<220> FEATURE:
<223> OTHER INFORMATION: Peptide 12 sequence as described in Figure 3

<400> SEQUENCE: 6

Gly Pro Lys Tyr Val Lys Gln Asn Thr Leu Lys Leu Ala Asn Thr
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Peptide 14 sequence as described in Figure 3

<400> SEQUENCE: 7

Cys Ala Ser Gly Arg Leu Lys Trp Arg Tyr Arg Arg Ile Arg
```

```
<210> SEQ ID NO 8
<211> LENGTH: 22
<212> TYPE: PRT
<213> ORGANISM: Artificial Sequence
<220> FEATURE:
<223> OTHER INFORMATION: Peptide 21 sequence as described in Figure 11

<400> SEQUENCE: 8

Val Asp Thr Gly Ser Gly Gly Gly Gly Gln Pro His Asp Thr Ala Pro
1               5                   10                  15

Arg Gly Ala Arg Lys Lys
            20

<210> SEQ ID NO 9
<211> LENGTH: 24
<212> TYPE: PRT
<213> ORGANISM: Artificial Sequence
<220> FEATURE:
<223> OTHER INFORMATION: Peptide functionalised by an alpha-oxoaldehyde

<400> SEQUENCE: 9

Ala Val Asp Thr Gly Ser Gly Gly Gly Gly Gln Pro His Asp Thr Ala
1               5                   10                  15

Pro Arg Gly Ala Arg Lys Lys Gln
            20

<210> SEQ ID NO 10
<211> LENGTH: 4
<212> TYPE: PRT
<213> ORGANISM: Artificial Sequence
<220> FEATURE:
<223> OTHER INFORMATION: Peptide functionalised by an alpha-oxoaldehyde
<220> FEATURE:
<221> NAME/KEY: MOD_RES
<222> LOCATION: (1)..(1)
<223> OTHER INFORMATION: Acetyl group

<400> SEQUENCE: 10

Lys Tyr Met Leu
1
```